United States Patent [19]

Hamprecht et al.

[11] Patent Number: 5,188,657
[45] Date of Patent: Feb. 23, 1993

[54] HERBICIDAL SULFONYLUREAS AND THEIR USE

[75] Inventors: Gerhard Hamprecht, Weinheim; Horst Mayer, Ludwigshafen; Karl-Otto Westphalen, Speyer; Helmut Walter, Obrigheim; Matthias Gerber, Mutterstadt; Klaus Grossmann; Wilhelm Rademacher, both of Limburgerhof, all of Fed. Rep. of Germany

[73] Assignee: BASF Aktiengesellschaft, Ludwigshafen, Fed. Rep. of Germany

[21] Appl. No.: 739,443

[22] Filed: Aug. 2, 1991

[30] Foreign Application Priority Data

Aug. 3, 1990 [DE] Fed. Rep. of Germany ....... 4024754

[51] Int. Cl.$^5$ .................. C07D 251/46; C07D 401/12; C07D 413/12; A01N 43/66
[52] U.S. Cl. .................................... 504/212; 544/211; 544/209; 544/113; 544/212; 544/208; 540/598; 504/191; 504/185; 504/178; 504/168; 504/213
[58] Field of Search .................... 71/93; 544/211, 209, 544/113, 212, 208; 540/598

[56] References Cited

U.S. PATENT DOCUMENTS

| | | | |
|---|---|---|---|
| 4,443,243 | 4/1984 | Forg et al. | 71/93 |
| 4,478,635 | 1/1983 | Meyer et al. | 71/92 |
| 4,518,776 | 5/1985 | Meyer et al. | 544/206 |
| 4,579,583 | 4/1986 | Föry et al. | 71/92 |
| 4,690,707 | 9/1987 | Föry et al. | 71/93 |
| 4,816,064 | 3/1989 | Konno et al. | 71/93 |
| 4,831,138 | 5/1989 | Lachhein | 544/320 |

FOREIGN PATENT DOCUMENTS

| | | |
|---|---|---|
| 1172253 | 8/1984 | Canada . |
| 1223591 | 6/1987 | Canada . |
| 0070804 | 1/1983 | European Pat. Off. . |
| 0084020 | 7/1983 | European Pat. Off. . |
| 0169815 | 1/1986 | European Pat. Off. . |
| 0336587 | 10/1989 | European Pat. Off. . |

OTHER PUBLICATIONS

Chemical Abstracts, vol. 109, entry 88185s (1988).
Chemical Abstracts, (1990), 112, 72315K "Synergistic Herbicides Containing a Triazine and an Acetanilide or a Dinitroaniline", Jiro et al.

Primary Examiner—John M. Ford
Attorney, Agent, or Firm—Oblon, Spivak, McClelland, Maier & Neustadt

[57] ABSTRACT

Substituted sulfonylureas of the formula I

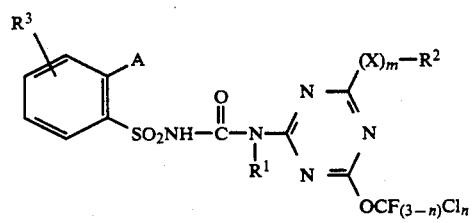

where n and m are each 0 or 1, $R^1$ is hydrogen, alkyl alkenyl or alkynyl, $R^2$ is halogen or trifluoromethyl when m is 0, or is alkyl, alkenyl or alkynyl when m is 1, or is trifluoromethyl or chlorodifluoromethyl when X is O or S and m is 1, X is O, S or N-$R^4$, $R^4$ is hydrogen or alkyl, $R^3$ is hydrogen, halogen, alkyl, haloalkyl or alkoxy, A is haloalkyl, halogen, cyano, nitro, alkoxy, alkylthio, alkylsulfinyl, alkylsulfonyl or a radical

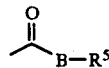

B is oxygen or an alkylimino group N-$R^6$; $R^5$ is hydrogen, unsubstituted or substituted alkyl or unsubstituted or substituted cycloalkyl or is alkenyl or alkynyl and $R^6$ is hydrogen or alkyl or, together with $R^5$, forms a $C_4$-$C_6$-alkylene chain in which a methylene group may be replaced by an oxygen atom or a $C_1$-$C_4$-alkylimino group, and their environmentally compatible salts, processes and intermediates for the preparation of the compounds I and their use as herbicides and bioregulators.

6 Claims, No Drawings

HERBICIDAL SULFONYLUREAS AND THEIR USE

The present invention relates to substituted sulfonylureas of the general formula I

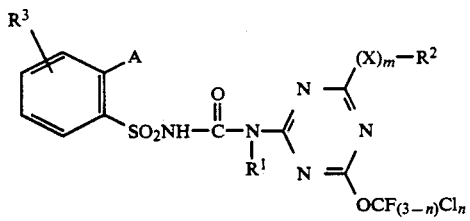

where
n and m are each 0 or 1;
$R^1$ is hydrogen, $C_1$-$C_4$-alkyl, $C_3$-$C_6$-alkenyl or $C_3$-$C_6$-alkynyl;
$R^2$ is halogen or trifluoromethyl when m is 0, or $C_1$-$C_4$-alkyl, $C_3$-$C_6$-alkenyl or $C_3$-$C_6$-alkynyl when m is 1, or trifluoromethyl or chlorodifluoromethyl when X is O or S and m is 1;
X is O, S or N-$R^4$, where $R^4$ is hydrogen or $C_1$-$C_4$-alkyl;
$R^3$ is hydrogen, halogen, $C_1$-$C_4$-alkyl, $C_1$-$C_4$-haloalkyl or $C_1$-$C_4$-alkoxy;
A is $C_1$-$C_4$-haloalkyl, halogen, cyano, nitro, $C_1$-$C_4$-alkoxy, $C_1$-$C_4$-alkylthio, $C_1$-$C_4$-alkylsulfinyl or -sulfonyl or a radical

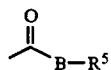

B is oxygen or an alkylimino group N-$R^5$;
$R^5$ is hydrogen, $C_1$-$C_6$-alkyl which may carry up to three of the following radicals: halogen, $C_1$-$C_4$-alkoxy, $C_1$-$C_4$-alkylthio, $C_1$-$C_4$-haloalkoxy, $C_2$-$C_4$-alkoxy-$C_1$- or -$C_2$-alkoxy, $C_3$-$C_7$-cycloalkyl and/or phenyl; $C_5$-$C_7$-cycloalkyl which may carry up to three $C_1$-$C_4$-alkyl groups; $C_3$-$C_6$-alkenyl or $C_3$-$C_6$-alkynyl, and
$R^6$ is hydrogen or $C_1$-$C_6$-alkyl or, together with $R^5$, forms a $C_4$-$C_6$-alkylene chain in which a methylene group may be replaced by an oxygen atom or a $C_1$-$C_4$-alkylimino group.

The present invention furthermore relates to a process for the preparation of the compounds I and their use as herbicides and intermediates for the preparation of sulfonylureas I.

EP-A-84 020 and 169 815 describe sulfonylureas which are substituted in the pyrimidine moiety by the difluoromethoxy or the bromotrifluoromethoxy radical. However, these compounds do not meet requirements owing to the unsatisfactory selectivity with respect to weeds. Correspondingly substituted triazines were unknown to date.

It is an object of the present invention to provide novel compounds from the class consisting of the sulfonyl-1,3,5-triazin-2-ylureas having improved herbicidal properties. We have found that this object is achieved by the sulfonylureas defined at the outset.

We have also found that the compounds of the formula I and their alkali metal and alkaline earth metal salts have good selectivity with respect to weeds in crops such as cereals and peanuts.

We have furthermore found chemically unique processes for the preparation of the compounds I. Compared with the prior art, the sulfonylureas I can be prepared in high yield and purity if substituted 2-amino-4-fluoroalkoxy-1,3,5-triazines of the general formula IIIa

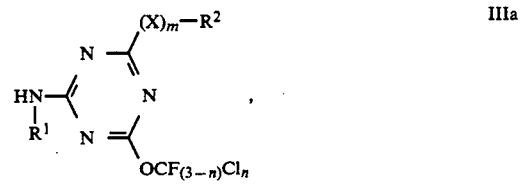

where m is 1, n is 0 or 1, $R^1$ is hydrogen, $C_1$-$C_4$-alkyl, $C_3$-$C_6$-alkenyl or $C_3$-$C_6$-alkynyl, $R^2$ is $C_1$-$C_4$-alkyl, $C_3$-$C_6$-alkenyl or $C_3$-$C_6$-alkynyl, X is O, S or N-$R^4$ and $R^4$ is hydrogen or $C_1$-$C_4$-alkyl, are used as starting materials.

The present invention therefore also relates to these intermediates and their preparation.

For the preparation of compounds which are halogen-substituted in the 1,3,5-triazine moiety ($R^2$=Hal, m=0), correspondingly substituted 2-amino-4-fluoroalkoxy-6-halo-1,3,5-triazines of the structure IIIb are used as starting materials (cf. scheme 2), the preparation of which forms the subject of the application Ser. No. 07/733,844, filed Jul. 22, 1991. 1,3,5-Triazine intermediates in which m is 0 and $R^2$ is trifluoromethyl are obtained in a similar manner, according to scheme 3.

The novel sulfonylureas of the formula I are obtainable by the routes A, B and C described in scheme 1:

A:  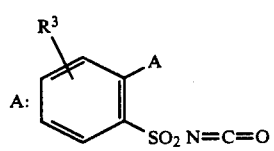   + 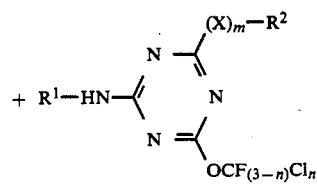

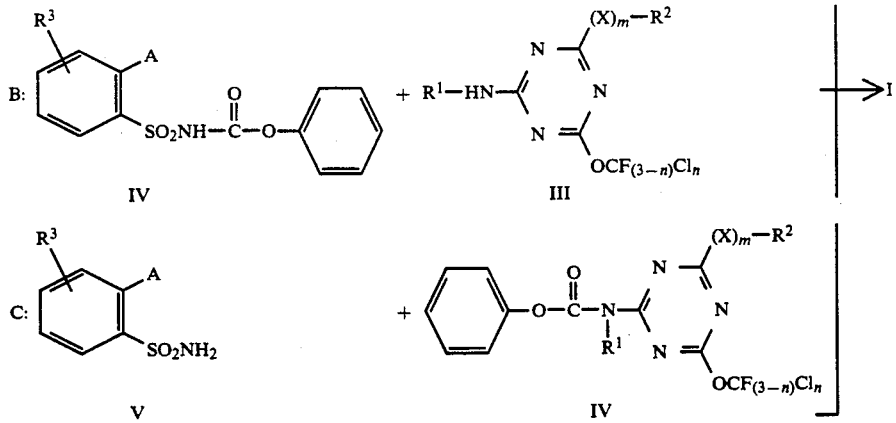

EMBODIMENT A

A sulfonyl isocyanate II is reacted with about the stoichiometric amount of a 2-amino-1,3,5-triazine derivative III in a conventional manner (EP-A-162 723) in an inert organic solvent at from 0° to 120° C., preferably from 10° to 100° C. The reaction can be carried out at atmospheric or superatmospheric pressure (up to 50 bar), preferably from 1 to 5 bar, continuously or batchwise. Suitable solvents are stated in the abovementioned literature.

EMBODIMENT B

A corresponding sulfonyl carbamate of the formula IV is reacted with a 2-amino-1,3,5-triazine derivative III in a conventional manner (EP-A-162 723) in an inert organic solvent at from 0° to 120° C., preferably from 10° to 100° C. Bases such as tertiary amines may be added, with the result that the reaction is accelerated and the product quality improved.

Examples of suitable bases for this purpose are tertiary amines, such as pyridine, the picolines, 2,4- and 2,6-lutidine, 2,4,6-collidine, p-dimethylaminopyridine, 1,4-diazabicyclo[2.2.2]octane (DABCO) and 1,8-diazabicyclo[5.4.0]undec-7-ene.

Advantageously used solvents are those stated in the literature and/or halohydrocarbons, such as dichloromethane and chlorobenzene, ethers, such as diethyl ether, tetrahydrofuran and dioxane, acetonitrile, dimethylformamide and/or esters, such as ethyl acetate, in an amount of from 100 to 4,000, preferably from 1,000 to 2,000, % by weight, based on the starting materials II, IV and V.

In connection with the preparation of the novel compounds, the 2-amino-1,3,5-triazine intermediates III are obtainable in the following advantageous manner:

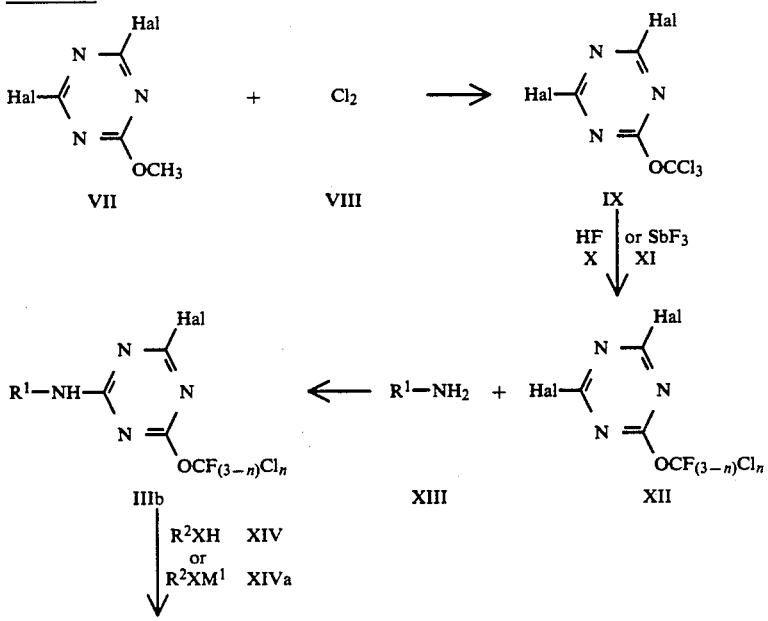

Scheme 2:

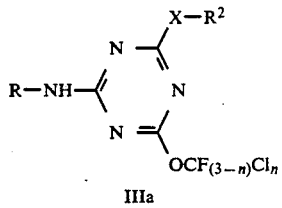

IIIa

The 2-amino-6-trifluoromethyl-1,3,5-triazine derivatives IIIc are obtained in a similar manner when 2,4-dihalo-6-trifluoromethyl-1,3,5-triazines are reacted according to scheme 3.

Scheme 3:

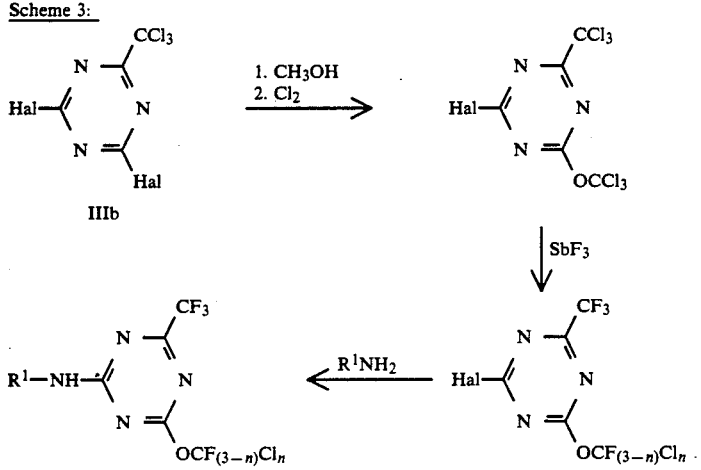

The intermediates IIId

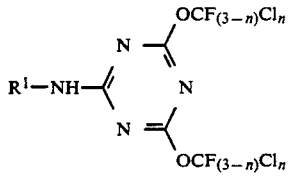

IIId are obtained starting from the intermediates XII in scheme 2 and with substitution of the halogen atom in the 4-position by the reaction sequence described in scheme 3 (1. CH$_3$OH, 2. Cl$_2$, 3. SbF$_3$), and subsequent reaction with R$^1$NH$_2$.

The chlorination of the 2-methoxy-1,3,5-triazine VII with chlorine VIII to give the trichloromethoxy-1,3,5-triazine IX is carried out, for example, at from 100° to 180° C.

Suitable chlorinating agents are elemental chlorine or chlorine-donating substances, such as sulfuryl chloride or phosphorus pentachloride. Chlorine can also be prepared in situ by oxidation of hydrochloric acid, for example with hydrogen peroxide.

The reaction can be carried out in the presence of an inert solvent, for example a chlorohydrocarbon, such as chlorobenzene, 1,2-, 1,3- or 1,4-dichlorobenzene, a nitro compound, such as nitrobenzene, a carboxylic acid, such as acetic acid or propionic acid, an anhydride, such as acetic anhydride, an acyl chloride, such as chloroacetyl chloride, α-chloropropionyl chloride or α,α-dichloropropionyl chloride, or an inorganic acid halide, such as phosphorous trichloride or phosphorus oxychloride, or preferably in the absence of a solvent, in the melt of the starting material VII.

The reaction may be accelerated by adding a free radical initiator; suitable initiation of this type is exposure to light, preferably UV light, or the addition of α,α'-azoisobutyronitrile, advantageously in an amount of from 0.2 to 7 mol %, based on the starting material VII. The reaction can also be accelerated by adding a catalyst; suitable catalysts are phosphorus pentachloride, advantageously in an amount of from 0.5 to 7 mol %, based on the starting material VII. In this case, the starting material VII is initially taken together with the catalyst and chlorination is then begun. Instead of the phosphorus pentachloride, it is also possible to add a starting component which forms this under the reaction conditions, for example phosphorus trichloride or yellow phosphorus, and then to begin chlorination.

Starting material VII can be reacted with chlorine in an almost stoichiometric amount or, preferably, in excess, advantageously with from 3.1 to 11, in particular from 3.3 to 5, moles of Cl$_2$ per equivalent of methoxy in the starting material VII. The reaction can be carried out at from 100° to 180° C., preferably from 120° to 150° C. under atmospheric or superatmospheric pressure, continuously or batchwise.

If chlorination is carried out at 1 bar, from 3.5 to 5 moles of chlorine gas per equivalent of methoxy in the starting material VII are advantageously used, corresponding to a chlorine conversion of from 91 to 60%. By suitable measures in terms of apparatus, for example by the use of moderate superatmospheric pressure, advantageously from 1 to 10 bar, or by the use of a bubble column, the chlorine conversion can be increased. The chlorine gas is advantageously allowed to come into contact with the organic phase for as long as possible, for example by stirring said phase vigorously or making it necessary for the chlorine gas to pass through a thick layer of the organic phase.

The reaction time is in general about 0.5-12 hours.

In a preferred embodiment of the process, the required amount of chlorine gas is passed into the liquid starting material VII in the course of from 0.5 to 12, preferably from 1 to 10, hours with thorough stirring, the initial temperature being from 120° to 130° C. and the temperature being increased continuously, if necessary utilizing the exothermic character of the reaction, so that the reaction is carried out at from 135° to 150° C. toward the end. In the case of larger reaction batches, the exothermic character must be taken into account by external cooling or suitable metering of the amount of chlorine; when the reaction dies down, the cooling bath is removed and further heating can, if necessary, be effected.

Working up and isolation of the end products are carried out in a conventional manner. For example, residues of hydrogen chloride, chlorine or catalyst can be removed from the hot organic phase by means of an inert gas; a crude product which is already very pure remains in high yield. It can be further purified by distillation or chromatography or used directly for further reactions.

The reaction of the trichloromethoxy-1,3,5-triazine IX with a halogen-exchanging agent is carried out, for example, at from 0° to 180° C.

Suitable halogen-exchanging agents are antimony trifluoride in the presence or absence of catalytic amounts of an antimony(V) salt or hydrogen fluoride.

An excess of from 1 to 200, preferably from 5 to 25, mol % of antimony trifluoride per trichloromethyl equivalent is advantageously used. The amount of antimony(V) salt catalyst is from 1 to 20, preferably from 5 to 18, mol % per trichloromethyl equivalent. The starting material XI is preferably metered into the mixture of the halogen-exchanging agent at from 90° to 130° C. and heating is then carried out for from 10 to about 240 minutes at from 110° to 180° C. The mixture is then worked up by distillation.

However, it is also possible to carry out the reaction continuously, to add the starting material XI at from 110° to 180° C. in the course of from 10 to about 240 minutes and at the same time to distill off, under reduced pressure, the resulting low boiling end product XIV. Traces of entrained antimony salts can be eliminated by extraction with concentrated hydrochloric acid.

If the reaction is carried out in the absence of catalysis by the antimony(V) salt or only small amounts, for example from 0.5 to 5 mol %, are used, and the amount of antimony trifluoride is reduced to 60-90 mol % per trichloromethyl equivalent, the halogen exchange stops at the chlorodifluoromethoxy stage.

Instead of antimony trifluoride, halogen exchange can also be effected using hydrogen fluoride at from 0° to 150° C., preferably from 40° to 120° C. For this purpose, an excess of from 300 to 700, preferably from 350 to 400, mol % of hydrogen fluoride per trichloromethyl equivalent is added to the starting material IX in an autoclave and the mixture is stirred for from 10 minutes to 10 hours. If necessary, the reaction can be accelerated in the manner described for the use of antimony trifluoride, by adding a catalyst, such as antimony pentachloride. After the pressure has been let down and the volatile constituents removed, working up is carried out in the manner described.

The reaction of the fluoromethoxy-1,3,5-triazine XII with an amine XIII is carried out, for example, at from −80° to 40° C.

In formula XIII, $R^1$ is hydrogen, $C_1-C_4$-alkyl, such as methyl, ethyl, n-propyl, isopropyl, n-butyl, secbutyl isobutyl or tert-butyl, $C_3$- or $C_4$-alkenyl, such as 2-propenyl, 2-methylethenyl, 2-butenyl, 3-butenyl, 1-methyl-2-propenyl or 2-methyl-2-propenyl, or $C_3$- or $C_4$-alkynyl, such as propargyl, 2-butynyl, 3-butynyl or 1-methyl-2-propynyl.

Among the amines which can be used, the following should be mentioned: ammonia, methylamine, ethylamine, n-propylamine, isopropylamine, n-butylamine, isobutylamine, sec-butylamine, tert-butylamine, 2-propenylamine, 2-methylethenylamine, 2-butenylamine, 3-butenylamine, 1-methyl- 2-propenylamine, 2-methyl-2-propenylamine, propargylamine, 2-butynylamine, 3-butynylamine and 1-methyl-2-propynylamine.

The 2-halo-1,3,5-triazines XII can be reacted with the amines XIII in an aprotic polar solvent at from −80° to 40° C., either the amine XIII being used in excess or an organic auxiliary base being employed.

The following solvents are suitable for the reaction of the 2,4-dihalo-1,3,5-triazine XII with the amine XIII: ethers, such as methyl tert-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, esters, such as ethyl acetate, n-butyl acetate and isobutyl acetate, and chlorohydrocarbons, such as methylene chloride, 1,1,2,2-tetrachloroethane, 1,1-dichloroethylene, 1,2-dichloroethane, chlorobenzene, 1,2-dichlorobenzene and 1-chloronaphthalene, and mixtures of these solvents.

The solvent is advantageously used in an amount of from 100 to 2,000, preferably from 400 to 1,200, % by weight, based on the starting material XII.

Advantageously, from 1.8 to 2.5, in particular from 1.95 to 2.2, mol equivalents, based on the starting material XII, of the amine XIII are added in the course of from 0.5 to 2 hours to a mixture of starting material XII in one of the abovementioned solvents at from −80° to 40° C., preferably from −70° to 25° C., stirring is carried out for up to 3 hours until the reaction is complete, and the mixture is then allowed to warm up to 25° C. for working up.

If only roughly stoichiometric amounts of the amine XIII are used, advantageously from 0.9 to 1.1 equivalents, based on the starting material XII, of an organic auxiliary base are employed. Suitable auxiliary bases are organic bases, such as trimethylamine, triethylamine, N-ethylisopropylamine, triisopropylamine, N,N-dimethylaniline, N,N-dimethylcyclohexylamine, N-methylpyrrolidine, pyridine, quinoline, α-, β- and γ-picoline, 2,4- and 2,6-lutidine and triethylenediamine.

The reaction can be carried out under atmospheric or superatmospheric pressure, continuously or batchwise.

For working up, the reaction mixture is extracted with water to remove the salts, and the organic phase is dried and purified, for example by chromatography. However, it is also possible directly to evaporate down the organic phase and to stir the residue with a solvent.

The novel 2-amino-4-fluoroalkoxy-1,3,5-triazines of the formula IIIa are advantagoeusly obtained by reacting a 2-amino-4-fluoroalkoxy-6-halo-1,3,5-triazine of the formula IIIb

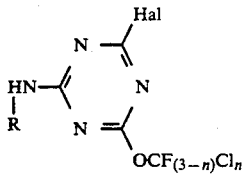

where Hal is fluorine, chlorine or bromine and $R^1$ and n have the abovementioned meanings, with a nucleophile of the formula XIV

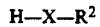 H—X—R²  XIV where X and R² have the abovementioned meanings, or with its salt.

Where 2-amino-4-fluoro-6-trifluoromethoxy-1,3,5-triazine and methylamine are used, the reaction can be described by the following scheme:

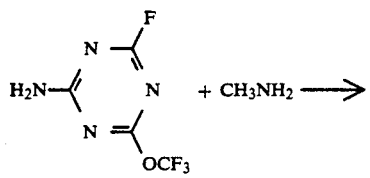

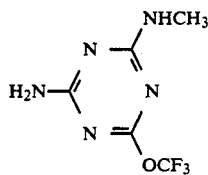

Where 2-amino-4-fluoro-6-chlorodifluoromethoxy-1,3,5-triazine and sodium methylate are used, the reaction can be represented by the following scheme:

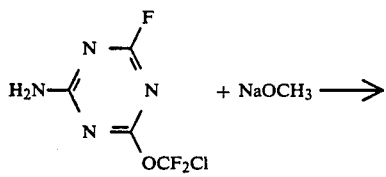

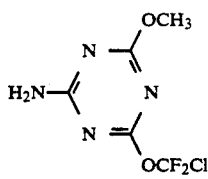

The process gives novel 2-amino-4-fluoroalkoxy-1,3,5-triazines in high yield and purity by a simple and economical method. Contrary to expectations, fluoroalkoxy groups are not substituted. Even the chlorine atom in the ether side chain is retained despite the alkaline reaction conditions. In view of the prior art (cf. for example EP-A-70 804), all these advantageous properties are surprising.

Preferred intermediates IIIa and accordingly preferred starting materials IIIb are those in whose formulae the substituents have the following meanings: $R^1$ and $R^2$ are each $C_1$-$C_4$-alkyl, such as methyl, ethyl, n-propyl, isopropyl, n-butyl, sec-butyl, isobutyl or tertbutyl, $C_3$- or $C_4$-alkenyl, such as 2-propenyl, 2-methylethenyl, 2-butenyl, 3-butenyl, 1-methyl-2-propenyl or 2-methyl-2-propenyl or $C_3$- or $C_4$-alkynyl, such as propargyl, 2-butynyl, 3-butynyl or 1-methyl-2-propynyl, and $R^1$ may furthermore be hydrogen, X is O, S or N-$R^4$, $R^4$ is hydrogen, methyl, ethyl, n-propyl, isopropyl, n-butyl, secbutyl, isobutyl or tert-butyl and n is 0 or 1.

The reaction of the 2-amino-4-fluoroalkoxy-1,3,5-triazine IIIb with a nucleophile XIV or with its salt XIVa is carried out, for example at from −80° to 80° C. Suitable nucleophiles XIV are ammonia, aliphatic amines, alcohols and thiols.

Among the amines which can be used as nucleophiles, the following should be mentioned: ammonia, methylamine, ethylamine, n-propylamine, isopropylamine, n-butylamine, isobutylamine, sec-butylamine, tert-butylamine, 2-propenylamine, 2-methylethenylamine, 2-butenylamine, 3-butenylamine, 1-methyl-2-propenylamine, 2-methyl-2-propenylamine, propargylamine, 2-butynylamine, 3-butynylamine and 1-methyl-2-propynylamine, dimethylamine, diethylamine, di-n-propylamine, di-n-butylamine, N-methylethylamine,N-ethyl-n-propylamine,N-methylallylamine and N-methylpropargylamine.

Among the alcohols which can be used as nucleophiles, the following should be mentioned: methanol, ethanol, n-propanol, isopropanol, n-butanol, isobutanol, sec-butanol, tert-butanol, 2-propenol, 2-methylethenol, 2-butenol, 3-butenol, 1-methyl-2-propenol, 2-methyl-2-propenol, propynol, 2-butynol, 3-butynol and 1-methyl-2-propynol.

Among the thiols which can be used as nucleophiles, the following should be mentioned: methanethiol, ethanethiol, n-propanethiol, isopropanethiol, n-butanethiol, isobutanethiol, sec-butanethiol, tert-butanethiol, 2-butenethiol, 2-methylethenethiol, 2-butenethiol, 3-butenethiol,1-methyl-2-propenethiol, 2-methyl-2-propenethiol, propynethiol, 2-butynethiol, 3-butynethiol and 1-methyl-2-propynethiol.

The 4-halo-1,3,5-triazines IIIb can be reacted with the amines XIV in an aprotic polar solvent at from −80° to +80° C., advantageously from −30° to +20° C., either the amine XIV being used in excess or an organic auxiliary base being employed.

The following solvents are suitable for the reaction of the 4-halo-1,3,5-triazine IIIb with the amine XIV: ethers, such as methyl tert-butyl ether, diethyl ether, ethyl propyl ether, n-butyl ethyl ether, di-n-butyl ether, diisobutyl ether, diisoamyl ether, diisopropyl ether, cyclohexyl methyl ether, tetrahydrofuran, 1,2-dimethoxyethane, diethylene glycol dimethyl ether and anisole, esters, such as ethyl acetate, n-butyl acetate and isobutyl acetate, and chlorohydrocarbons, such as methylene chloride, 1,1,2,2-tetrachloroethane, 1,1-dichloroethylene, 1,2-dichloroethane, chlorobenzene, 1,2-dichlorobenzene and 1-chloronaphthalene, and mixtures of these solvents.

The solvent is advantageously used in an amount of from 100 to 2,000, preferably from 400 to 1,200, % by weight, based on the starting material IIIb.

Advantageously, from 1.8 to 2.5, in particular from 1.95 to 2.2, mol equivalents, based on the starting material IIIb, are added in the course of from 0.5 to 2 hours to a mixture of starting material IIIb in one of the abovementioned solvents at from −80° to 80° C., preferably from −30° to 25° C., stirring is carried out until the reaction is complete (up to 3 hours) and the mixture is then allowed to warm up to 25° C. for working up.

If only roughly stoichiometric amounts of the amine XIV are used, from 0.9 to 1.1 equivalents, based on the starting material IIIb, of an organic auxiliary base must advantageously be used. Suitable auxiliary bases are organic bases, such as trimethylamine, triethylamine, N-ethyldiisopropylamine,triisopropylamine,N,N-dimethylaniline, N,N-dimethylcyclohexylamine, N-methylpyrrolidine, pyridine, quinoline, α-, β- and γ-picoline, 2,4- and 2,6-lutidine and triethylenediamine.

If the reaction is carried out using alcohols or thiols, it is possible to adopt a procedure similar to the reaction procedure described for amines. Advantageously, the nucleophile is added in an amount of 0.9 to 1.3 mol equivalents, based on the starting material IIIb, in the course of from 0.5 to 2 hours, together with one of the abovementioned auxiliary bases, to a mixture of starting material IIIb in one of the abovementioned solvents at from $-30°$ to 20° C., stirring is carried out until the reaction is complete (up to 3 hours) and the mixture is then allowed to warm up to 25° C. for working up.

In addition to the stated solvents, other suitable solvents are ketones, eg. acetone or methyl ethyl ketone, dipolar aprotic solvents, eg. acetonitrile, dimethylformamide, dimethylacetamide, dimethyl sulfoxide, N-methylpyrrolidone or 1,3-dimethylimidazolin-2-one, aromatics, eg. benzene, toluene or xylene, and corresponding mixtures. Where alcohols are used as nucleophiles, they can advantageously be employed directly as solvents. Salts of alcohols or thiols, which make it possible to dispense with the use of an organic auxiliary base, are particularly preferred. They are prepared in a known manner using alkali metals or alkaline earth metals or metal hydrides, eg. NaH, KH, $CaH_2$ or LiH.

The reaction can be carried out at atmospheric or superatmospheric pressure, continuously or batchwise.

For working up, the reaction mixture is extracted with water to remove the salts and the organic phase is dried and purified, for example by chromatography. However, the reaction products are generally sufficiently pure, so that all that is necessary is to filter off the solution from the precipitated salt and to evaporate down the organic phase.

Examples of preferred intermediates of the formula IIIa are:
2-amino=4=methoxy-6-trifluoromethoxy-1,3,5-triazine
2-amino-4-chlorodifluoromethoxy-6-methoxy-1,3,5-triazine
2-amino-4-ethoxy-6-trifluoromethoxy-1,3,5-triazine
2-amino-4-chlorodifluoromethoxy-6-ethoxy-1,3,5-triazine
2-amino-4-allyloxy-6-trifluoromethoxy-1,3,5-triazine
2-amino-4-allyloxy-6-chlorodifluoromethoxy-1,3,5-triazine
2-amino-4-methylthio-6-trifluoromethoxy-1,3,5-triazine
2-amino-4-chlorodifluoromethoxy-6-methylthio-1,3,5-triazine
2-amino-4-ethylthio-6-trifluoromethoxy-1,3,5-triazine
2-amino-4-chlorodifluoromethoxy-6-ethylthio-1,3,5-triazine
2-amino-4-methylamino-6-trifluoromethoxy-1,3,5-triazine
2-amino-4-chlorodifluoromethoxy-6-methylamino-1,3,5-triazine
2-amino-4-ethylamino-6-trifluoromethoxy-1,3,5-triazine
2-amino-4-chlorodifluoromethoxy-6-ethylamino-1,3,5-triazine
2-amino-4-dimethylamino-6-trifluoromethoxy-1,3,5-triazine
2-amino-4-chlorodifluoromethoxy-6-dimethylamino-1,3,5-triazine
4-methoxy-2-methylamino-6-trifluoromethoxy-1,3,5-triazine
4-chlorodifluoromethoxy-6-methoxy-2-methylamino-1,3,5-triazine
4-ethoxy-2-methylamino-6-trifluoromethoxy-1,3,5-triazine
4-chlorodifluoromethoxy-6-ethoxy-2-methylamino-1,3,5-triazine
2,4-bismethylamino-6-trifluoromethoxy-1,3,5-triazine
4-chlorodifluoromethoxy-2,6-bismethylamino-1,3,5-triazine
4-ethylamino-2-methylamino-6-trifluoromethoxy-1,3,5-triazine
4-chlorodifluoromethoxy-6-ethylamino-2-methylamino-1,3,5-triazine
4-dimethylamino-2-methylamino-6-trifluoromethoxy-1,3,5-triazine
4-chlorodifluoromethoxy-6-dimethylamino-2-methylamino-1,3,5-triazine

EMBODIMENT C

A sulfonamide of the formula V is reacted with about the stoichiometric amount of a phenyl carbamate VI in a conventional manner (EP-A-141 777) in an inert organic solvent at from 0° to 120° C., preferably from 20° to 100° C. The reaction can be carried out at atmospheric or superatmospheric pressure (up to 50 bar), preferably from 1 to 5 bar, continuously or batchwise.

Suitable solvents in addition to those stated in the literature cited above are, for example, nitro hydrocarbons, such as nitroethane and nitrobenzene, nitriles, such as acetonitrile and benzonitrile, esters, such as ethyl acetate, amides, such as dimethylformamide, and/or ketones, such as acetone. The reaction is preferably carried out in ethyl acetate as the solvent and using pyridine or one of the abovementioned tertiary amines as the base.

The sulfonamides required as starting materials of the formula V can be prepared from substituted anthranilic esters by the Meerwein reaction and subsequent reaction with ammonia.

Compounds of the formula I where $R^5$ is hydrogen are obtained by hydrolyzing an ester of the formula I where $R^5$ is $C_1$-$C_6$-alkyl. The hydrolysis is carried out using not less than twice the amount of a base, such as sodium hydroxide or potassium hydroxide, advantageously in a solvent mixture containing from 2 to 8 times the amount of methanol and from 10 to 40 times the amount of water, the amounts being based on the weight of the corresponding ester of the formula I, at from 30° to 80° C. in the course of from 1 to 20 hours. The sulfonamidocarboxylic acid of the formula I is precipitated by acidification.

With regard to the biological activity, preferred compounds of the formula I are those in which the substituents have the following meanings:

$R^1$ is hydrogen or methyl, $R^2$ is fluorine, chlorine, bromine or trifluoromethyl (m=0), or methyl, ethyl, n-propyl or isopropyl (m=1), $R^3$ is hydrogen, fluorine, chlorine, bromine, methyl, methoxy or trifluoromethyl, X is oxygen, sulfur or an amino group $-NR^4$, $R^4$ is hydrogen, methyl or ethyl, A is chlorine, trifluoromethyl, CN, NO$_2$, methyl, ethyl, methoxy, ethoxy, methylthio, ethylthio, methylsulfinyl, methylsulfonyl, ethylsulfonyl, a carboxylate group or a carboxamide group, R$^5$ is C$_1$–C$_6$-alkyl, in particular C$_1$–C$_4$-alkyl, such as methyl, ethyl, n-propyl or isopropyl, C$_2$–C$_4$-alkenyl, such as allyl, crotyl or but-1-en-3-yl, C$_2$–C$_4$-alkynyl, such as propargyl, but-1-yn-3-yl or but-2-ynyl, haloalkyl, such as 2-chloroethyl, 2-chloro-n-propyl, 3-chloro-n-propyl, 1-chlorobut-2-yl, 2-chloroisobutyl, 4-chloro-n-butyl, chloro-tert-butyl, 3-chloroprop-2-yl or 2,2,2-trifluoroethyl, alkoxyalkyl, such as 2-methoxyethyl, 3-ethoxyethyl, 3-methoxy-n-propyl, 2-methoxy-n-propyl, 3-methoxy-n-butyl, 1-methoxybut-2-yl, methoxy-tert-butyl, 2-methoxy-n-butyl or 4-methoxy-n-butyl, alkoxyalkoxyalkyl, such as 2-methoxyethoxymethyl, 2-(ethoxy)-ethoxymethyl, 2-(propoxy)-ethoxymethyl, 2-methoxyethoxyethyl, 2-(ethoxy)-ethoxyethyl or 2-(methoxymethoxy)-ethyl, haloalkoxyalkyl, such as 2-($\beta$-chloroethoxy)-ethyl, 3-($\beta$-chloroethoxy)-n-propyl or 3-($\gamma$-chloro-n-propoxy)-n-propyl, or cycloalkyl, such as cyclopentyl or cyclohexyl, R$^6$ is hydrogen or C$_1$–C$_6$-alkyl, in particular C$_1$–C$_4$-alkyl, such as methyl, ethyl, n-propyl, isopropyl or n-butyl or, together with R$^5$, forms tetramethylene, pentamethylene, hexamethylene, ethyleneoxyethylene or ethylene-N-methyliminoethylene, and n is 0 or 1.

Suitable salts of the compounds of the formula I are agriculturally useful salts, for example alkali metal salts, such as the potassium or sodium salt, alkaline earth metal salts, such as calcium, magnesium or barium salt, manganese salts, copper salts, zinc salts or iron salts, and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

The novel herbicidal and growth-regulating compounds I or the agents containing them can be used, for example, in the form of directly sprayable solutions, powders, suspensions, including concentrated aqueous, oil or other suspensions and dispersions, emulsions, oil dispersions, pastes, dusting agents, broadcasting agents or granules, by spraying, atomizing, dusting, broadcasting or pouring. The application forms depend on the intended uses; they should in any case ensure very fine distribution of the novel active ingredients.

The compounds I are suitable in general for the preparation of directly sprayable solutions, emulsions, pastes or oil dispersions. Suitable inert additives are mineral oil fractions having a medium to high boiling point, such as kerosene or diesel oil, and coal tar oils and oils of vegetable or animal origin, aliphatic, cyclic and aromatic hydrocarbons, eg. toluene, xylene, paraffin, tetrahydronaphthalene, alkylated naphthalenes or their derivatives, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substrates as such or in solution in an oil or solvent can be homogenized in water by means of wetting agents, adherents, dispersants or emulsifiers. However, it is also possible to prepare concentrates which consist of active substance, wetting agents, adherents, dispersants or emulsifiers and possibly solvents or oil and which are suitable for dilution with water.

Suitable surfactants are the alkali metal, alkaline earth metal and ammonium salts of aromatic sulfonic acids, for example lignin-, phenol-, naphthalene- and dibutylnaphthalenesulfonic acid, and of fatty acids, alkylsulfonates, alkylarylsulfonats, alkylsulfates, lauryl ether sulfates and fatty alcohol sulfates, and salts of sulfated hexa-, hepta- and octadecanols, and of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ethers, ethoxylated isooctyl-, octyl or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, broadcasting agents and dusting agents can be prepared by mixing or milling the active substances together with a solid carrier.

Granules, for example coated, impregnated and homogeneous granules, can be prepared by binding the active ingredients to solid carriers. Solid carriers are mineral earths, such as silica gel, silicas, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate or ureas, and vegetable products, such as grain flours, bark meal, wood meal and nutshell meal, cellulosic powders and other solid carriers.

The formulations contain from 0.1 to 95, preferably from 0.5 to 90, % by weight of active ingredient. The active ingredients are used in a purity of from 90 to 100%, preferably from 95 to 100% (according to NMR spectrum).

The novel compounds I can be formulated, for example, as follows:

I. 90 parts by weight of compound No. 5.019 are mixed with 10 parts by weight of N-methyl-$\alpha$-pyrrolidone, and a solution which is suitable for use in the form of very small drops is obtained.

II. 20 parts by weight of compound No. 5.019 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of the calcium salt of dodecylbenzenesulfonic acid and 5 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

III. 20 parts by weight of compound No. 5.019 are dissolved in a mixture which consists of 40 parts by weight of cyclohexanone, 30 parts by weight of isobutanol, 20 parts by weight of the adduct of 7 moles of ethylene oxide with 1 mole of isooctylphenol and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

IV. 20 parts by weight of active ingredient No. 5.019 are dissolved in a mixture which consists of 25 parts by weight of cyclohexanone, 65 parts by weight of a mineral oil fraction boiling within a range from 210° to 280° C. and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

V. 20 parts by weight of active ingredient No. 5.019 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 5.019 are mixed with 97 parts by weight of finely divided kaolin. A dusting agent which contains 3% by weight of the active ingredient is obtained in this manner.

VII. 30 parts by weight of active ingredient No. 5.019 are thoroughly mixed with a mixture of 92 parts by weight of silica gel powder and 8 parts by weight of liquid paraffin, which was sprayed onto the surface of this silica gel. A formulation of the active ingredient having good adhesion is obtained in this manner.

VIII. 20 parts by weight of active ingredient No. 5.019 are thoroughly mixed with 2 parts by weight of calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

The herbicidal and growth-regulating agents or the active ingredients can be applied by the preemergence or postemergence method. If the active ingredients are less well tolerated by certain crops, it is possible to use application methods in which the herbicides are sprayed with the aid of the sprayers in such a way that, as far as possible, the herbicides do not come into contact with the leaves of the sensitive crops while the active ingredients reach the leaves of undesirable plants growing underneath or the uncovered soil surface (postdirected, lay-by).

The application rates of active ingredient when used as herbicides are from 0.001 to 2, preferably from 0.01 to 1 kg/ha of active substance, depending on the aim of control, the season, the target plants and the state of growth.

The compounds of the formula I can influence virtually all stages of development of a plant in different ways and are therefore used as growth regulators. The wide range of activity of the plant growth regulators depends in particular a) on the plant species and variety,
b) on the time of application, based on the state of development of the plant, and on the season,
c) on the place and method of application (eg. seed dressing, soil treatment, foliage application or trunk injection in the case of trees),
d) on climatic factors, eg. temperature, amount of precipitation and also length of day and light intensity,
e) on the soil quality (including fertilizer application),
f) on the formulation or application form of the active ingredient and finally
g) on the concentrations in which the active substance is used.

Of the various possible applications of the novel plant growth regulators of the formula I in cultivation, in agriculture and in horticulture, a few are mentioned below.

A. The vegetative growth of the plants can be greatly inhibited using the compounds which can be employed according to the invention, this manifesting itself in particular in a reduction in the growth in length. The treated plants accordingly have stunted growth; a darker leaf coloration is also observed.

Reduced intensity of growth of grasses along road edges, hedges, canal banks and on lawn areas, such as parks, sports grounds and orchards, ornamental lawns and airfields, proves advantageous in practice, enabling labor-intensive and costly cutting of lawns to be reduced.

The increase in the strength of crops susceptible to lodging, such as cereals, corn, sunflowers and soybean, is also of economic interest. The resulting shortening and strengthening of the stem reduces or eliminates the danger of lodging (of bending) of plants under unfavorable weather conditions before the harvest.

The use of growth regulators for inhibiting the growth in length and for changing the time of ripening of cotton is also important. This permits completely mechanized harvesting of this important crop.

In the case of fruit trees and other trees, growth regulators make it possible to reduce the costs of cutting. In addition, the alternance of fruit trees can be broken by growth regulators.

By using growth regulators, it is also possible to increase or inhibit the lateral branching of the plants. This is of interest when, for example in tobacco plants, it is intended to inhibit the formation of side shoots in favor of leaf growth.

It is also possible considerably to increase the resistance to frost by means of growth regulators, for example in winter rape. On the one hand, the growth in length and the development of a leaf or plant mass which is too luxurious (and hence particularly susceptible to frost) are inhibited. On the other hand, the young rape plants are held back in the vegetative state of development after sowing and before the onset of the winter frosts, in spite of favorable growth conditions. This also eliminates the frost risk to plants which tend to exhibit a premature decline in the inhibition of blooming and to go over into the generative phase. In other crops too, for example winter cereals, it is advantageous if, by treatment with novel compounds, the stocks are well tillered in fall but do not begin winter with too luxurious a growth. This makes it possible to avoid high sensitivity to frost and, owing to the relatively small leaf or plant mass, attack by various diseases (for example fungal disease). The inhibition of vegetative growth furthermore permits denser planting of the soil in the case of many crops, so that a greater yield can be achieved, based on the soil area.

B. The growth regulators make it possible to achieve greater yields of both plant parts and plant ingredients. For example, it is possible to induce the growth of greater quantities of buds, blooms, leaves, fruits, seeds, roots and tubers, to increase the content of sugar in sugar beets, sugar cane and citrus fruits, to increase the protein content in cereals or soybean or to stimulate greater latex flow in rubber trees.

The compounds of the formula I can result in increased yields by intervening in the plant metabolism or by promoting or inhibiting vegetative and/or generative growth.

C. Finally, plant growth regulators make it possible both to shorten or lengthen the development stages and to accelerate or retard ripening of the harvested plant parts before or after harvesting.

For example, facilitating harvesting is of economic interest, this being permitted by concentrated dropping or a reduction in the adherence to the tree in the case of citrus fruits, olives or other species and varieties of pomes, drupes and hardshell fruit. The same mechanism, ie. promotion of the formation of abscission tissue between the fruit or leaf part and the shoot part of the plant, is also essential for readily controllable defoliation of crops such as cotton.

D. Growth regulators can furthermore be used to reduce the water consumption of plants. This is particularly important for agricultural areas which have to be artificially irrigated at high expense, for example in arid or semiarid regions. By using the novel substances, it is possible to reduce the intensity of irrigation and hence to carry out more economical farming. The influence of growth regulators results in better utilization of the available water because, inter alia, the extent of opening of the stomata is reduced, a thicker epidermis and cuticula are formed, root penetration of the soil is improved and the microclimate of the crop is advantageously affected by more compact growth.

The growth regulators of the formula I which are to be used according to the invention can be fed to the crops both via the seed (as seed dressings) and via the soil, ie. through the root and, particularly preferably, via the foliage by spraying.

Owing to the good toleration by plants, the application rate can be greatly varied.

In view of the wide range of application methods, the novel compounds or agents containing them can be used in a large number of crops for eliminating undesirable plants.

| List of crops: | |
|---|---|
| Botanical name | Common name |
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Brassica napus var. napus | rapeseed |
| Brassica napus var. napobrassica | swedes |
| Brassica rapa var. silvestris | beets |
| Camellia sinensis | tea plants |
| Carthamus tinctorius | safflower |
| Carya illinoinensis | pecan trees |
| Citrus limon | lemons |
| Cirus sinensis | orange trees |
| Coffea arabica (Coffea canephora, Coffea liberica) | coffee plants |
| Cucumis sativus | cucumbers |
| Cynodon dactylon | Bermudagrass in turf and lawns |
| Daucus carota | carrots |
| Elaeis guineensis | oil palms |
| Fragaria vesca | strawberries |
| Glycine max | soybeans |
| Gossypium hirsutum (Gossypium arboreum Gossypium herbaceum | cotton |
| Gossypium vitifolium) | |
| Helianthus annuus | sunflowers |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus vulgaris | snapbeans, green beans, dry beans |
| Picea abies | Norway spruce |
| Pinus spp. | pine trees |
| Pisum sativum | English peas |
| Prunus avium | cherry trees |
| Prunus persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

To broaden the action spectrum and to achieve synergistic effects, the novel compounds I can be mixed with a large number of other herbicidal or growth-regulating active ingredients and applied together with them. Examples of suitable components for the mixture are diazine, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives, quinolinecarboxylic acid derivatives, sulfonylurea derivatives, aryloxy- and hetaryloxyphenoxypropionic acids and their salts, esters and amides, and others.

It may also be useful to apply the compounds I, alone or in combination with other herbicides, also as a mixture with other crop protection agents, for example with pesticides or agents for controlling phytopathogenic fungi or bacteria. The miscibility with mineral salt solutions which are used for eliminating nutrient and trace element deficiencies is also of interest. Nonphytotoxic oils and oil concentrates may also be added.

EXAMPLES OF SYNTHESES

I Preparation of the intermediates

EXAMPLE I.1

2,4-Difluoro-6-trichloromethoxy-1,3,5-triazine

A stream of chlorine gas was passed into a mixture of 300 g (2.041 mol) of 2,4-difluoro-6-methoxy-1,3,5-triazine and 0.3 g of α,α'-azoisobutyronitrile at 130° C. and with exposure to UV radiation, so that a temperature of from 140° to 145° C. resulted in the course of 2 hours. After checking the progress of the reaction by NMR spectroscopy, gassing with chlorine was continued for a further 3 hours at from 135° to 140° C. with external heating.

After the solution had been filtered off under suction from the resulting precipitate and the filtrate had been distilled under reduced pressure, 444 g (87% of theory) of the title compound of boiling point 40°–46° C. 0.3 mbar were obtained.

EXAMPLE I.2

2,4-Difluoro-6-trifluoromethoxy-1,3,5-triazine

Half of 210 g (0.838 mol) of 2,4-difluoro-6-trichloromethoxy-1,3,5-triazine was added to a mixture of 187.4 g (1.048 mol) of antimony trifluoride and 35.2 g (0.117 mol) of antimony pentachloride, initially at 110° C. while stirring, so that a temperature of 125° C. was initially established; with the resulting refluxing, external heating was necessary on further addition. Stirring was continued for one hour at from 125° to 130° C. and a fraction boiling at from 100° to 105° C. was distilled off over a 25 cm packed column. After the reaction had died down, the remaining half of the trichloromethoxy compound was added dropwise in the course of 30 minutes and the fraction passing over at from 100° to 105° C. was distilled off continuously. The total reaction time was 3 hours. 134.4 g (79.8% of theory) of the title compound of $n_D^{24} = 1.3650$ were obtained.

EXAMPLE I.3

6-Chlorodifluoromethoxy-2,4-difluoro-1,3,5-triazine 210 g (0.838 mol) of 2,4-difluoro-6-trichloromethoxy-1,3,5-triazine were added to 110 g (0.614 mol) of antimony trifluoride in the course of 10 minutes while stirring at 110° C. After the addition of 3/4 of 9.38 g (0.0313 mol) of antimony pentachloride, the mixture was heated to 145° C. and stirred for 1 hour. The remaining catalyst was added and stirring was continued for a further 2 hours, 20 g (11.8% of theory) of 2,4-difluoro-6-trifluoromethoxy-1,3,5-triazine being obtained as a low boiling fraction over a 30 cm packed column at from 95° to 105° C. The distillation residue was distilled without a column and gave 94.8 g (52% of theory) of the title compound of boiling point 125°–130° C. and $n_D^{24} = 1.4042$.

EXAMPLE I.4

2,4-Dichloro-6-trifluoromethoxy-1,3,5-triazine 52 g (0.183 mol) of 2,4-difluoro-6-trichloromethoxy-1,3,5-triazine were added to a mixture of 40.9 g (0.229 mol) of antimony trifluoride and 7.03 g (0.0234 mol) of antimony pentachloride in the course of 5 minutes while stirring at 90° C., the temperature increasing to 180° C. Stirring was continued for a further 20 minutes at from 170° to 180° C., after which the crude product was distilled off at 90°–103° C./70 mbar. Further distillation gave 32.3 g (75.5% of theory) of the title compound of boiling point 165°–173° C.

EXAMPLE I.5

2Amino-4-fluoro-6-trifluoromethoxy-1,3,5-triazine 4.4 g (0.259 mol) of ammonia gas were passed into a mixture of 26.0 g (0.1293 mol) of 2,4-difluoro-6-trifluoromethoxy-1,3,5-triazine in 100 ml of tetrahydrofuran in the course of 45 minutes at from −70° to −65° C., while stirring. Stirring was continued for 2 hours at −70° C. and overnight while warming up to 22° C. The mixture was evaporated down under reduced pressure, after which the residue was stirred with water and the product was filtered off under suction, washed and dried to give 22 g 85.9% of theory) of the title compound of melting point 138°–139° C.

EXAMPLE I.6

2,4-Bismethylamino-6-trifluoromethoxy-1,3,5-triazine and
2-methylamino-4-fluoro-6-trifluoromethoxy-1,3,5-triazine 5.9 g (0.189 mol) of gaseous methylamine were passed into a mixture of 19.0 g (0.0945 mol) of 2,4-difluoro-6-trifluoromethoxy-1,3,5-triazine in 100 ml of diethyl ether at −70° C. in the course of 30 minutes, while stirring. Stirring was continued for 2 hours at −70° C. and overnight while warming up to 22° C. The reaction mixture was evaporated down under reduced pressure, the residue was taken up in methylene chloride and the solution was washed with water. After drying, fractional chromatography was carried out over a silica gel column, 5.0 g (25% of theory) of 2-methylamino-4-fluoro-6-trifluoromethoxy-1,3,5-triazine of melting point 68°–72° C. was obtained in the first two fractions. In the further fractions 4 to 7, 10.7 g (51% of theory) of the more sparingly soluble 2,4-bismethylamino-6-trifluoromethoxy-1,3,5-triazine of melting point 150°–152° C. were isolated.

EXAMPLE I.7

2-Amino-4-chlorodifluoromethoxy-6-fluoro-1,3,5-triazine and
2,4-diamino-6-chlorodifluoromethoxy-1,3,5-triazine 7.8 g (0.46 mol) of ammonia were passed into a mixture of 50.0 g (0.23 mol) of 2,4-difluoro-6-chlorodifluoromethoxy-1,3,5-triazine in 150 ml of tetrahydrofuran in the course of 45 minutes at −70° C., while stirring. Stirring was continued for 2 hours at −70° C. and overnight while warming up to 22° C. The reaction mixture was evaporated down under reduced pressure and the residue was washed with water and dried. The reaction product was then washed onto a silica gel column with methylene chloride and eluted with the same solvent. 21.5 g (43.6% of theory) of 2-amino-4-fluoro-6-chlorodifluoromethoxy-1,3,5-triazine of melting point 131°–133° C. were obtained in fractions 1 to 8.

The more sparingly soluble 2,4-diamino-6-chlorodifluoromethoxy-1,3,5-triazine (11.2 g, 23% of theory) of melting point 114° C. was then obtained in fractions 9 to 14 by eluting with ethyl acetate.

EXAMPLE I.8

2-Chlorodifluoromethoxy-4-fluoro-6-methylamino-1,3,5-triazine and
2,4-bismethylamino-6-chlorodifluoromethoxy1,3,5-triazine 5.2 g (0.166 mol) of methylamine were passed into a mixture of 18.1 g (0.083 mol) of 4-difluorochloromethoxy-2,6-difluoro-1,3,5-triazine and solvent in the course of 20 minutes at −70° C., while stirring. Stirring was continued for 2 hours at −70° C. and overnight while warming up to 22° C. The reaction mixture was evaporated down under reduced pressure, the residue was taken up in methylene chloride and the solution was washed with water and dried. Chromatography over silica gel gave 5.5 g (29% of theory) of 2-chlorodifluoromethoxy-4-fluoro-6-methylamino-1,3,5-triazine of melting point 62-64° C. in the first fractions. 8.7 g (44% of theory) of 2,4-bismethylamino-6-chlorodifluoromethoxy-1,3,5-triazine of melting point 118°–120° C. were isolated from subsequent fractions.

II Preparation of intermediates IIIa

EXAMPLE II.1

2Amino-4-methoxy-6-trifluoromethoxy-1,3,5-triazine 9.1 g (0.05 mol) of 30% strength sodium methylate were added to a mixture of 10 g (0.05 mol) of 2-amino-4-fluoro-6-trifluoromethoxy-1,3,5-triazine in 100 ml of methanol at 0° C. in the course of 15 minutes, while stirring. Stirring was carried out for one hour at 0° C., after which the mixture was evaporated down under reduced pressure, the residue was taken up in methylene chloride and the solution was extracted with water. Drying and evaporation gave 10.5 g (99% of theory) of the title compound of melting point 96°–101° C.

EXAMPLE II.2

2-Amino-4-chlorodifluoromethoxy-6-methoxy-1,3,5-triazine 8.4 g (0.047 mol) of 30% strength sodium methylate were added to a mixture of 10 g (0.047 mol) of 2-amino-4-chlorodifluoromethoxy-6-fluoro-1,3,5-triazine in 100 ml of methanol at 0° C. in the course of 15 minutes, while stirring. Stirring was carried out for one hour at 0° C., after which the mixture was evaporated down under reduced pressure, the residue was taken up in methylene chloride and the solution was extracted with water. Drying and evaporation gave 10.4 g (98.5% of theory) of the title compound of melting point 109°–111° C.

EXAMPLE II.3

2-Amino-4-methoxy-6-trifluoromethoxy-1,3,5-triazine 2.3 g (0.093 mol) of 97% strength sodium hydride were added a little at a time to 300 ml of ethanol at from 20 to 35° C. and stirring was carried out until dissolution was complete, which took 15 minutes. 18.5 g (0.093 mol) of 2-amino-4-fluoro-6-trifluoromethoxy-1,3,5-triazine were then added at 0° C. in the course of 10 minutes, while stirring and stirring was continued for 1 hour at 0° C. and overnight at 22° C. The mixture was evaporated down under reduced pressure, after which the residue was taken up in methylene chloride and the solution was extracted with water and dried. Evaporation gave 17.9 g (85.9% of theory) of the title compound of melting point 69°–91° C.

EXAMPLE II.4

2-Amino-4-chlorodifluoromethoxy-6-ethoxy-1,3,5-triazine 1.2 g (0.047 mol) of 97% strength sodium hydride were added a little at a time to 150 ml of ethanol at from 20 to 35° C. and stirring was carried out until dissolution occurred, which took 15 minutes. 10.0 g (0.047 mol) of 2-amino-4-chlorodifluoromethoxy-6-fluoro-1,3,5-triazine were then added at 0° C., while stirring, and stirring was continued for 1 hour at 0° C. and overnight at 22° C. The solution was evaporated down under reduced pressure, after which the residue was taken up in methylene chloride and the solution was extracted with water and dried. Evaporation gave 10.6 g (94.6% of theory) of the title compound of melting point 63°–65° C.

EXAMPLE II.5

2-Amino-4-methylamino-6-trifluoromethoxy-1,3,5-triazine 3.5 g (0.111 mol) of gaseous methylamine were passed into a solution of 11 g (0.055 mol) of 2-amino-4-fluoro-6-trifluoromethoxy-1,3,5-triazine in 150 ml of tetrahydrofuran at 0° C. in the course of 20 minutes, while stirring. Stirring was continued for one hour at 0° C. and overnight at 22° C. The reaction mixture was evaporated down under reduced pressure and the residue was stirred with water and dried. 10.8 g (93.1% of theory) of the title compound of melting point 155°–157° C. (decomposition) were obtained.

EXAMPLE II.6

2-Amino-4-chlorodifluoromethoxy-6-methylamino-1,3,5-triazine 2.9 g (0.093 mol) of gaseous methylamine were passed into a solution of 10 g (0.047 mol) of 2-amino-4-chlorodifluoromethoxy-6-fluoro-1,3,5-triazine in 150 ml of diethyl ether at 0° C. in the course of 20 minutes, while stirring. Stirring was continued for one hour at 0° C. and overnight at 22° C. Washing with water, drying and evaporating down gave 9.4 g (89.5% of theory) of the title compound of melting point 143° C. (decomposition).

EXAMPLE II.7

2-Amino-4-dimethylamino-6-trifluoromethoxy-1,3,5-triazine 5.0 g (0.111 mol) of gaseous dimethylamine were passed into a solution of 11 g (0.055 mol) of 2-amino-4-fluoro-6-trifluoromethoxy-1,3,5-triazine in 150 ml of tetrahydrofuran at 0° C. in the course of 20 minutes, while stirring. Stirring was continued for one hour at 0° C. and overnight at 22° C. Evaporating down, washing with water and drying gave 9.9 g (80.7% of theory) of the title compound of melting point 114°–118° C. (decomposition).

EXAMPLE II.8

2-Amino-4-chlorodifluoromethoxy-6-dimethylamino-1,3,5-triazine 4.2 g (0.093 mol) of dimethylamine were passed into a solution of 10 g (0.047 mol) of 2-amino-4-chlorodifluoromethoxy-6-fluoro-1,3,5-triazine in 150 ml of diethyl ether at 0° C. in the course of 20 minutes, while stirring. Stirring was continued for one hour at 0° C. and overnight at 22° C. Washing with water, drying and evaporating down gave 9.8 g (87.8% of theory) of the title compound of melting point 130°–133° C. (decomposition).

III Preparation of the sulfonylurea compounds I

EXAMPLE III.1

Methyl 2-(((4-Methoxy-6-trifluoromethoxy-1,3,5-triazin-2-yl)-aminocarbonyl)-aminosulfonyl)-benzoate 3.6 g (0.015 mol) of 2-carbomethoxybenzosulfonyl isocyanate in 4 ml of 1,2-dichloroethane were added to a mixture of 3.15 g (0.015 mol) of 2-amino-4-methoxy-6- trifluoromethoxy-1,3,5-triazine in 150 ml of 1,2-dichloroethane at 22° C. in the course of 5 minutes, while stirring, and stirring was continued for 12 hours at 22° C. The reaction mixture was evaporated down under reduced pressure, the residue was crystallized with 1:1 methyl tert-butyl ether/petroleum ether and the crystals were filtered off under suction and washed with petroleum ether. 5.1 g (75.4% of theory) of the title compound of melting point 149° C. (decomposition) were obtained. (Active Ingredient Example 5.001).

EXAMPLE III.2

2-(((4-Methoxy-6-trifluoromethoxy-1,3,5-triazin-2-yl)-aminocarbonyl)-aminosulfonyl)-benzoic acid methyl ester sodium salt 1.8 g (0.004 mol) of the compound from Example III.1 were suspended in 30 ml of methanol, and 0.72 g (0.004 mol) of 30% strength sodium methylate solution was added at from 10 to 15° C., while stirring. After 10 minutes, the clear solution was evaporated down under reduced pressure, 1.9 g (100% of theory) of the title compound of melting point 118° C. (decomposition) being obtained (Active Ingredient Example 5.019).

EXAMPLE III.3

Ethyl 2-(((4-methylamino-6-trifluoromethoxy-1,3,5-triazin-2-yl)-aminocarbonyl)-aminosulfonyl)-benzoate 3.1 g (0.012 mol) of 2-carboethoxybenzosulfonyl isocyanate in 3 ml of methylene chloride were added to a mixture of 2.5 g (0.012 mol) of 2-amino-4-methylamino-6-trifluoromethoxy-1,3,5-triazine in 150 ml of methylene chloride at 22° C. in the course of 10 minutes, while stirring, and stirring was continued for 30 hours at 22° C. The reaction mixture was evaporated down under reduced pressure and the product was stirred with methyl tert-butyl ether and filtered off under suction. Further washing with methanol and drying gave 3.8 g (67.4% of theory) of the title compound of melting point 182°-184° C. (decomposition) (Active Ingredient Example 7.003).

The methods described in the Examples below were used for obtaining further compounds of the formula I with appropriate modification of the starting compounds; the compounds obtained are shown in the Tables below, together with the physical data; compounds without these data can be synthesized from the corresponding substances in a similar manner. Because of their close structural relationships with the compounds prepared and investigated, they are likely to have the same action.

TABLE 1

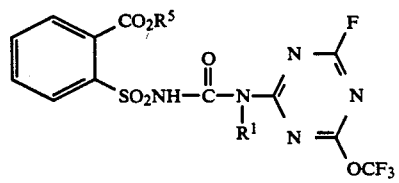

| No. | R¹ | R⁵ | mp. (°C.) | |
|---|---|---|---|---|
| 1.001 | H | CH₃ | 163 | |
| 1.002 | CH₃ | CH₃ | | |
| 1.003 | H | CH₂CH₃ | | |
| 1.004 | CH₃ | CH₂CH₃ | | |
| 1.005 | H | (CH₂)₂CH₃ | | |

TABLE 1-continued

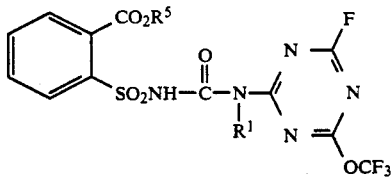

| No. | R¹ | R⁵ | mp. (°C.) | |
|---|---|---|---|---|
| 1.006 | CH₃ | (CH₂)₂CH₃ | | |
| 1.007 | H | CH(CH₃)₂ | | |
| 1.008 | H | CH₂—CH=CH₂ | | |
| 1.009 | H | CH₂—CH=CH—CH₃ | | |
| 1.010 | H | CH₂—C≡C—CH₃ | | |
| 1.011 | H | (CH₂)₂Cl | | |
| 1.012 | CH₃ | (CH₂)₂Cl | | |
| 1.013 | H | (CH₂)₂OCH₃ | | |
| 1.014 | H | (CH₂)₂O(CH₂)₂OCH₃ | | |
| 1.015 | H | Cyclopentyl | | |
| 1.016 | H | Cyclohexyl | | |
| 1.017 | H | CH₂CF₃ | | |
| 1.018 | H | (CH₂)₂SCH₃ | | |
| 1.019 | H | CH₃ | | Na salt |
| 1.020 | CH₃ | CH₃ | | Na salt |
| 1.021 | H | CH₂CH₃ | | Na salt |
| 1.022 | CH₃ | CH₂CH₃ | | Na salt |
| 1.023 | H | (CH₂)₂CH₃ | | Na salt |
| 1.024 | H | (CH₂)₂Cl | | Na salt |

TABLE 2

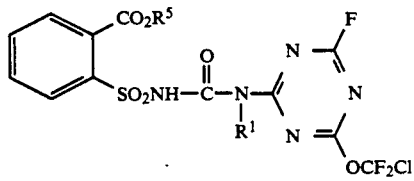

| No. | R¹ | R⁵ | mp. (°C.) | |
|---|---|---|---|---|
| 2.001 | H | CH₃ | | |
| 2.002 | CH₃ | CH₃ | | |
| 2.003 | H | CH₂CH₃ | | |
| 2.004 | CH₃ | CH₂CH₃ | | |
| 2.005 | H | (CH₂)₂CH₃ | | |
| 2.006 | CH₃ | (CH₂)₂CH₃ | | |
| 2.007 | H | CH(CH₃)₂ | | |
| 2.008 | H | CH₂—CH=CH₂ | | |
| 2.009 | H | CH₂—CH=CH—CH₃ | | |
| 2.010 | H | CH₂—C≡C—CH₃ | | |
| 2.011 | H | (CH₂)₂Cl | | |
| 2.012 | CH₃ | (CH₂)₂Cl | | |
| 2.013 | H | (CH₂)₂OCH₃ | | |
| 2.014 | H | (CH₂)₂O(CH₂)₂OCH₃ | | |
| 2.015 | H | Cyclopentyl | | |
| 2.016 | H | Cyclohexyl | | |
| 2.017 | H | CH₂CF₃ | | |
| 2.018 | H | (CH₂)₂SCH₃ | | |
| 2.019 | H | CH₃ | | Na salt |
| 2.020 | CH₃ | CH₃ | | Na salt |
| 2.021 | H | CH₂CH₃ | | Na salt |
| 2.022 | CH₃ | CH₂CH₃ | | Na salt |
| 2.023 | H | (CH₂)₂CH₃ | | Na salt |
| 2.024 | H | (CH₂)₂Cl | | Na salt |

TABLE 3

Structure: phenyl ring with $CO_2R^5$ and $SO_2NH-C(=O)-N(R^1)-$ triazine (Cl, OCF$_3$ substituents)

| No. | R$^1$ | R$^5$ | mp. (°C.) | |
|---|---|---|---|---|
| 3.001 | H | CH$_3$ | | |
| 3.002 | CH$_3$ | CH$_3$ | | |
| 3.003 | H | CH$_2$CH$_3$ | | |
| 3.004 | CH$_3$ | CH$_2$CH$_3$ | | |
| 3.005 | H | (CH$_2$)$_2$CH$_3$ | | |
| 3.006 | CH$_3$ | (CH$_2$)$_2$CH$_3$ | | |
| 3.007 | H | CH(CH$_3$)$_2$ | | |
| 3.008 | H | CH$_2$—CH=CH$_2$ | | |
| 3.009 | H | CH$_2$—CH=CH—CH$_3$ | | |
| 3.010 | H | CH$_2$—C≡C—CH$_3$ | | |
| 3.011 | H | (CH$_2$)$_2$Cl | | |
| 3.012 | CH$_3$ | (CH$_2$)$_2$Cl | | |
| 3.013 | H | (CH$_2$)$_2$OCH$_3$ | | |
| 3.014 | H | (CH$_2$)$_2$O(CH$_2$)$_2$OCH$_3$ | | |
| 3.015 | H | Cyclopentyl | | |
| 3.016 | H | Cyclohexyl | | |
| 3.017 | H | CH$_2$CF$_3$ | | |
| 3.018 | H | (CH$_2$)$_2$SCH$_3$ | | |
| 3.019 | H | CH$_3$ | | Na salt |
| 3.020 | CH$_3$ | CH$_3$ | | Na salt |
| 3.021 | H | CH$_2$CH$_3$ | | Na salt |
| 3.022 | CH$_3$ | CH$_2$CH$_3$ | | Na salt |
| 3.023 | H | (CH$_2$)$_2$CH$_3$ | | Na salt |
| 3.024 | H | (CH$_2$)$_2$Cl | | Na salt |

TABLE 4

Structure: phenyl ring with $CO_2R^5$ and $SO_2NH-C(=O)-N(R^1)-$ triazine (Cl, OCF$_2$Cl substituents)

| No. | R$^1$ | R$^5$ | mp. (°C.) | |
|---|---|---|---|---|
| 4.001 | H | CH$_3$ | | |
| 4.002 | CH$_3$ | CH$_3$ | | |
| 4.003 | H | CH$_2$CH$_3$ | | |
| 4.004 | CH$_3$ | CH$_2$CH$_3$ | | |
| 4.005 | H | (CH$_2$)$_2$CH$_3$ | | |
| 4.006 | CH$_3$ | (CH$_2$)$_2$CH$_3$ | | |
| 4.007 | H | CH(CH$_3$)$_2$ | | |
| 4.008 | H | CH$_2$—CH=CH$_2$ | | |
| 4.009 | H | CH$_2$—CH=CH—CH$_3$ | | |
| 4.010 | H | CH$_2$—C≡C—CH$_3$ | | |
| 4.011 | H | (CH$_2$)$_2$Cl | | |
| 4.012 | CH$_3$ | (CH$_2$)$_2$Cl | | |
| 4.013 | H | (CH$_2$)$_2$OCH$_3$ | | |
| 4.014 | H | (CH$_2$)$_2$O(CH$_2$)$_2$OCH$_3$ | | |
| 4.015 | H | Cyclopentyl | | |
| 4.016 | H | Cyclohexyl | | |
| 4.017 | H | CH$_2$CF$_3$ | | |
| 4.018 | H | (CH$_2$)$_2$SCH$_3$ | | |
| 4.019 | H | CH$_3$ | | Na salt |
| 4.020 | CH$_3$ | CH$_3$ | | Na salt |
| 4.021 | H | CH$_2$CH$_3$ | | Na salt |
| 4.022 | CH$_3$ | CH$_2$CH$_3$ | | Na salt |
| 4.023 | H | (CH$_2$)$_2$CH$_3$ | | Na salt |
| 4.024 | H | (CH$_2$)$_2$Cl | | Na salt |

TABLE 5

Structure: phenyl ring with $CO_2R^5$ and $SO_2NH-C(=O)-N(R^1)-$ triazine (OCH$_3$, OCF$_3$ substituents)

| No. | R$^1$ | R$^5$ | mp. (°C.) | |
|---|---|---|---|---|
| 5.001 | H | CH$_3$ | 149 decomp. | |
| 5.002 | CH$_3$ | CH$_3$ | | |
| 5.003 | H | CH$_2$CH$_3$ | | |
| 5.004 | CH$_3$ | CH$_2$CH$_3$ | | |
| 5.005 | H | (CH$_2$)$_2$CH$_3$ | | |
| 5.006 | CH$_3$ | (CH$_2$)$_2$CH$_3$ | | |
| 5.007 | H | CH(CH$_3$)$_2$ | | |
| 5.008 | H | CH$_2$—CH=CH$_2$ | | |
| 5.009 | H | CH$_2$—CH=CH—CH$_3$ | | |
| 5.010 | H | CH$_2$—C≡C—CH$_3$ | | |
| 5.011 | H | (CH$_2$)$_2$Cl | | |
| 5.012 | CH$_3$ | (CH$_2$)$_2$Cl | | |
| 5.013 | H | (CH$_2$)$_2$OCH$_3$ | | |
| 5.014 | H | (CH$_2$)$_2$O(CH$_2$)$_2$OCH$_3$ | | |
| 5.015 | H | Cyclopentyl | | |
| 5.016 | H | Cyclohexyl | | |
| 5.017 | H | CH$_2$CF$_3$ | | |
| 5.018 | H | (CH$_2$)$_2$SCH$_3$ | | |
| 5.019 | H | CH$_3$ | 118 decomp. | Na salt |
| 5.020 | CH$_3$ | CH$_3$ | | Na salt |
| 5.021 | H | CH$_2$CH$_3$ | | Na salt |
| 5.022 | CH$_3$ | CH$_2$CH$_3$ | | Na salt |
| 5.023 | H | (CH$_2$)$_2$CH$_3$ | | Na salt |
| 5.024 | H | (CH$_2$)$_2$Cl | | Na salt |

TABLE 6

Structure: phenyl ring with $CO_2R^5$ and $SO_2NH-C(=O)-N(R^1)-$ triazine (OCH$_3$, OCF$_2$Cl substituents)

| No. | R$^1$ | R$^5$ | mp. (°C.) | |
|---|---|---|---|---|
| 6.001 | H | CH$_3$ | 128-135 | |
| 6.002 | CH$_3$ | CH$_3$ | | |
| 6.003 | H | CH$_2$CH$_3$ | | |
| 6.004 | CH$_3$ | CH$_2$CH$_3$ | | |
| 6.005 | H | (CH$_2$)$_2$CH$_3$ | | |
| 6.006 | CH$_3$ | (CH$_2$)$_2$CH$_3$ | | |
| 6.007 | H | CH(CH$_3$)$_2$ | | |
| 6.008 | H | CH$_2$—CH=CH$_2$ | | |
| 6.009 | H | CH$_2$—CH=CH—CH$_3$ | | |
| 6.010 | H | CH$_2$—C≡C—CH$_3$ | | |
| 6.011 | H | (CH$_2$)$_2$Cl | | |
| 6.012 | CH$_3$ | (CH$_2$)$_2$Cl | | |
| 6.013 | H | (CH$_2$)$_2$OCH$_3$ | | |
| 6.014 | H | (CH$_2$)$_2$O(CH$_2$)$_2$OCH$_3$ | | |
| 6.015 | H | Cyclopentyl | | |
| 6.016 | H | Cyclohexyl | | |
| 6.017 | H | CH$_2$CF$_3$ | | |
| 6.018 | H | (CH$_2$)$_2$SCH$_3$ | | |
| 6.019 | H | CH$_3$ | 135 decomp. | Na salt |
| 6.020 | CH$_3$ | CH$_3$ | | Na salt |
| 6.021 | H | CH$_2$CH$_3$ | | Na salt |
| 6.022 | CH$_3$ | CH$_2$CH$_3$ | | Na salt |
| 6.023 | H | (CH$_2$)$_2$CH$_3$ | | Na salt |
| 6.024 | H | (CH$_2$)$_2$Cl | | Na salt |

TABLE 7

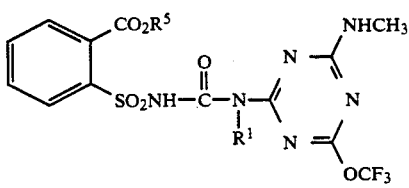

| No. | R¹ | R⁵ | mp. (°C.) | |
|---|---|---|---|---|
| 7.001 | H | CH₃ | 162 decomp. | |
| 7.002 | CH₃ | CH₃ | | |
| 7.003 | H | CH₂CH₃ | 182-184 decomp. | |
| 7.004 | CH₃ | CH₂CH₃ | | |
| 7.005 | H | (CH₂)₂CH₃ | | |
| 7.006 | CH₃ | (CH₂)₂CH₃ | | |
| 7.007 | H | CH(CH₃)₂ | | |
| 7.008 | H | CH₂—CH=CH₂ | | |
| 7.009 | H | CH₂—CH=CH—CH₃ | | |
| 7.010 | H | CH₂—C≡C—CH₃ | | |
| 7.011 | H | (CH₂)₂Cl | | |
| 7.012 | CH₃ | (CH₂)₂Cl | | |
| 7.013 | H | (CH₂)₂OCH₃ | | |
| 7.014 | H | (CH₂)₂O(CH₂)₂OCH₃ | | |
| 7.015 | H | Cyclopentyl | | |
| 7.016 | H | Cyclohexyl | | |
| 7.017 | H | CH₂CF₃ | | |
| 7.018 | H | (CH₂)₂SCH₃ | | |
| 7.019 | H | CH₃ | 155-160 decomp. | Na salt |
| 7.020 | CH₃ | CH₃ | | Na salt |
| 7.021 | H | CH₂CH₃ | | Na salt |
| 7.022 | CH₃ | CH₂CH₃ | | Na salt |
| 7.023 | H | (CH₂)₂CH₃ | | Na salt |
| 7.024 | H | (CH₂)₂Cl | | Na salt |

TABLE 8

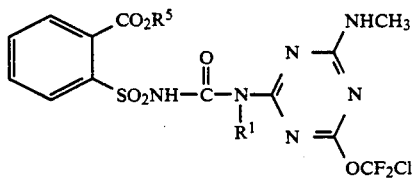

| No. | R¹ | R⁵ | mp. (°C.) | |
|---|---|---|---|---|
| 8.001 | H | CH₃ | 159 decomp. | |
| 8.002 | CH₃ | CH₃ | | |
| 8.003 | H | CH₂CH₃ | | |
| 8.004 | CH₃ | CH₂CH₃ | | |
| 8.005 | H | (CH₂)₂CH₃ | | |
| 8.006 | CH₃ | (CH₂)₂CH₃ | | |
| 8.007 | H | CH(CH₃)₂ | | |
| 8.008 | H | CH₂—CH=CH₂ | | |
| 8.009 | H | CH₂—CH=CH—CH₃ | | |
| 8.010 | H | CH₂—C≡C—CH₃ | | |
| 8.011 | H | (CH₂)₂Cl | | |
| 8.012 | CH₃ | (CH₂)₂Cl | | |
| 8.013 | H | (CH₂)₂OCH₃ | | |
| 8.014 | H | (CH₂)₂O(CH₂)₂OCH₃ | | |
| 8.015 | H | Cyclopentyl | | |
| 8.016 | H | Cyclohexyl | | |
| 8.017 | H | CH₂CF₃ | | |
| 8.018 | H | (CH₂)₂SCH₃ | | |
| 8.019 | H | CH₃ | 175-179 decomp. | Na salt |
| 8.020 | CH₃ | CH₃ | | Na salt |
| 8.021 | H | CH₂CH₃ | | Na salt |
| 8.022 | CH₃ | CH₂CH₃ | | Na salt |
| 8.023 | H | (CH₂)₂CH₃ | | Na salt |
| 8.024 | H | (CH₂)₂Cl | | Na salt |

TABLE 9

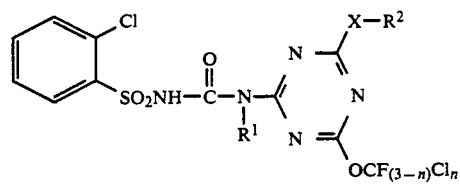

| No. | R¹ | X | R² | n | mp. (°C.) |
|---|---|---|---|---|---|
| 9.001 | H | — | F | 0 | |
| 9.002 | H | — | Cl | 0 | |
| 9.003 | CH₃ | — | F | 0 | |
| 9.004 | CH₃ | — | Cl | 0 | |
| 9.005 | H | — | F | 1 | |
| 9.006 | H | — | Cl | 1 | |
| 9.007 | CH₃ | — | F | 1 | |
| 9.008 | CH₃ | — | Cl | 1 | |
| 9.009 | H | — | F | 0 | Na salt |
| 9.010 | H | — | Cl | 0 | Na salt |
| 9.011 | H | O | CH₃ | 0 | 165 decomp. |
| 9.012 | H | O | CH₃ | 1 | |
| 9.013 | CH₃ | O | CH₃ | 0 | |
| 9.014 | CH₃ | O | CH₃ | 1 | |
| 9.015 | CH₃ | O | CH₃ | 0 | Na salt |
| 9.016 | CH₃ | O | CH₃ | 1 | Na salt |
| 9.017 | H | NH | CH₃ | 0 | 149 decomp. |
| 9.018 | H | NH | CH₃ | 1 | |
| 9.019 | H | NCH₃ | CH₃ | 0 | 194 decomp. |
| 9.020 | H | NCH₃ | CH₃ | 1 | |
| 9.021 | CH₃ | NCH₃ | CH₃ | 0 | |
| 9.022 | H | O | CH₃ | 0 | Na salt |
| 9.023 | H | NCH₃ | CH₃ | 0 | 168 decomp. Na salt |

TABLE 10

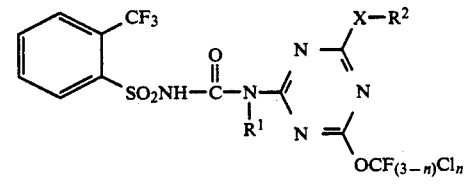

| No. | R¹ | X | R² | n | mp. (°C.) |
|---|---|---|---|---|---|
| 10.001 | H | — | F | 0 | |
| 10.002 | H | — | Cl | 0 | |
| 10.003 | H | — | F | 1 | |
| 10.004 | H | — | Cl | 1 | |
| 10.005 | H | O | CH₃ | 0 | |
| 10.006 | H | O | CH₃ | 1 | 133 |
| 10.007 | H | NH | CH₃ | 0 | 197 |
| 10.008 | H | NH | CH₃ | 1 | |
| 10.009 | CH₃ | NH | CH₃ | 0 | |
| 10.010 | CH₃ | NH | CH₃ | 1 | |
| 10.011 | H | O | CH₃ | 0 | 173 Na salt |
| 10.012 | H | NCH₃ | CH₃ | 0 | 174 Na salt |
| 10.013 | H | NCH₃ | CH₃ | 0 | 162 |
| 10.014 | H | NH | CH₃ | 0 | 175 Na salt |

TABLE 11

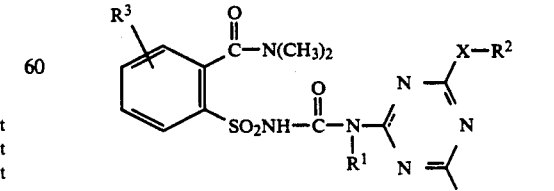

| No. | R¹ | X | R² | R³ | n | mp. (°C.) |
|---|---|---|---|---|---|---|
| 11.001 | H | — | F | — | 0 | |

TABLE 11-continued

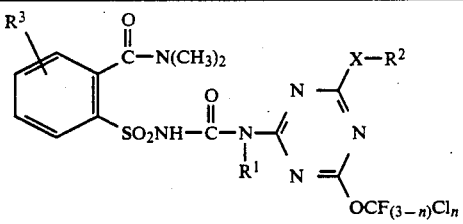

| No. | R¹ | X | R² | R³ | n | mp. (°C.) |
|---|---|---|---|---|---|---|
| 11.002 | H | — | Cl | — | 0 | |
| 11.003 | H | — | F | — | 1 | |
| 11.004 | H | — | Cl | — | 1 | |
| 11.005 | H | O | CH₃ | — | 0 | |
| 11.006 | H | O | CH₃ | 3-F | 1 | |
| 11.007 | H | NH | CH₃ | — | 0 | |
| 11.008 | H | NH | CH₃ | — | 1 | |
| 11.009 | H | O | CH₃ | 5-Cl | 0 | |
| 11.010 | H | O | CH₃ | 5-Cl | 1 | |

TABLE 12

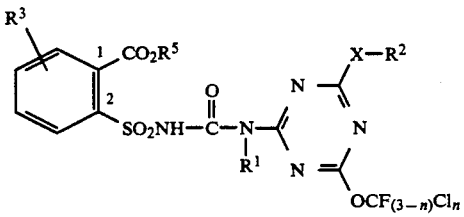

| No. | R¹ | X | R² | R³ | R⁵ | n | mp. (°C.) | |
|---|---|---|---|---|---|---|---|---|
| 12.001 | H | — | F | 3-F | CH₃ | 0 | | |
| 12.002 | H | — | Cl | 3-F | CH₃ | 0 | | |
| 12.003 | H | — | F | 3-F | CH₃ | 1 | | |
| 12.004 | H | — | Cl | 3-F | CH₃ | 1 | | |
| 12.005 | H | O | CH₃ | 3-F | CH₃ | 0 | | |
| 12.006 | H | O | CH₃ | 3-F | CH₃ | 1 | | |
| 12.007 | H | O | CH₃ | 5-Cl | CH₃ | 0 | | |
| 12.008 | H | O | CH₃ | 5-Cl | CH₃ | 1 | | |
| 12.009 | H | — | F | 5-Cl | CH₃ | 0 | | |
| 12.010 | H | — | F | 5-Cl | CH₃ | 1 | | |
| 12.011 | H | — | Cl | 5-Cl | CH₃ | 0 | | |
| 12.012 | H | — | Cl | 5-Cl | CH₃ | 1 | | |
| 12.013 | H | — | F | 6-CH₃ | CH₃ | 0 | | |
| 12.014 | H | — | F | 6-CH₃ | CH₃ | 1 | | |
| 12.015 | H | — | Cl | 6-CH₃ | CH₃ | 0 | | |
| 12.016 | H | — | Cl | 6-CH₃ | CH₃ | 1 | | |
| 12.017 | H | O | CH₃ | 6-CH₃ | CH₃ | 0 | | |
| 12.018 | H | O | CH₃ | 6-CH₃ | CH₃ | 1 | | |
| 12.019 | H | NH | CH₃ | 6-CH₃ | CH₃ | 0 | | |
| 12.020 | H | NH | CH₃ | 6-CH₃ | CH₃ | 1 | | |
| 12.021 | CH₃ | NH | CH₃ | 6-CH₃ | CH₃ | 0 | | |
| 12.022 | H | NH | CH₃ | 6-CH₃ | CH₃ | 0 | | Na salt |
| 12.023 | H | — | CF₃ | — | CH₃ | 0 | | |
| 12.024 | H | — | CF₃ | — | CH₃ | 0 | | |
| 12.025 | CH₃ | — | CF₃ | — | CH₃ | 0 | | |
| 12.026 | H | — | CF₃ | — | CH₃ | 1 | | |
| 12.027 | H | N—CH₃ | CH₃ | — | CH₃ | 0 | 172 decomp. | |
| 12.028 | H | N—CH₃ | CH₃ | — | CH₃ | 0 | 170–175 decomp. | Na salt |
| 12.029 | H | N—CH₃ | CH₃ | 6-CH₃ | CH₃ | 0 | | |
| 12.030 | H | N—CH₃ | CH₃ | 6-CH₃ | CH₃ | 1 | | |
| 12.031 | H | N—CH₃ | CH₃ | — | CH₃ | 0 | | |
| 12.032 | H | N—CH₃ | CH₃ | — | CH₃ | 1 | 158 decomp. | |
| 12.033 | H | O | C₂H₅ | — | CH₃ | 0 | 160–164 | |
| 12.034 | H | O | C₂H₅ | — | CH₃ | 0 | | Na salt |
| 12.035 | H | O | C₂H₅ | — | CH₃ | 1 | 83–86 decomp. | |
| 12.036 | CH₃ | O | C₂H₅ | — | CH₃ | 1 | | Na salt |
| 12.037 | H | O | C₂H₅ | 6-CH₃ | CH₃ | 0 | | |
| 12.038 | H | O | C₂H₅ | 5-Cl | CH₃ | 0 | | |
| 12.039 | CH₃ | O | C₂H₅ | 5-Cl | CH₃ | 0 | | |
| 12.040 | H | O | C₂H₅ | 5-Cl | CH₃ | 1 | | |
| 12.041 | H | O | CH₃ | — | C₂H₅ | 0 | | |
| 12.042 | H | O | CH₃ | — | C₂H₅ | 0 | | Na salt |
| 12.043 | H | O | CH₃ | — | C₂H₅ | 1 | | |
| 12.044 | H | O | C₂H₅ | 5-Cl | CH₃ | 0 | | Na salt |
| 12.045 | H | O | CH₃ | 3-Cl | CH₃ | 0 | | |
| 12.046 | H | O | CH₃ | 3-Cl | CH₃ | 0 | | Na salt |
| 12.047 | H | O | CH₃ | 4-Cl | CH₃ | 0 | | |
| 12.048 | H | O | CH₃ | 4-Cl | CH₃ | 0 | | Na salt |
| 12.049 | H | O | CH₃ | 3-Cl | CH₃ | 1 | | |
| 12.050 | H | O | CH₃ | 3-Cl | CH₃ | 1 | | Na salt |
| 12.051 | H | NH | CH₃ | 3-Cl | CH₃ | 0 | | |
| 12.052 | H | NH | CH₃ | 3-Cl | CH₃ | 0 | | Na salt |
| 12.053 | H | NH | CH₃ | 3-Cl | CH₃ | 1 | | |
| 12.054 | H | NH | CH₃ | 3-Cl | CH₃ | 1 | | Na salt |
| 12.055 | H | NCH₃ | CH₃ | 3-Cl | CH₃ | 0 | | |
| 12.056 | H | NCH₃ | CH₃ | 3-Cl | CH₃ | 0 | | Na salt |
| 12.057 | H | NCH₃ | CH₃ | 3-Cl | CH₃ | 1 | | |

TABLE 12-continued

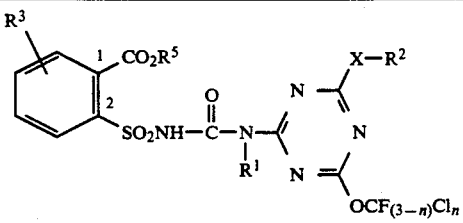

| No. | R¹ | X | R² | R³ | R⁵ | n | mp. (°C.) | |
|---|---|---|---|---|---|---|---|---|
| 12.058 | H | NCH₃ | CH₃ | 3-Cl | CH₃ | 1 | | Na salt |
| 12.059 | CH₃ | NCH₃ | CH₃ | 3-Cl | CH₃ | 0 | | |
| 12.060 | H | — | F | 3-Cl | CH₃ | 0 | | |
| 12.061 | H | — | F | 3-Cl | CH₃ | 0 | | Na salt |
| 12.062 | H | — | F | 3-Cl | CH₃ | 1 | | |
| 12.063 | H | — | F | 3-Cl | CH₃ | 1 | | Na salt |
| 12.064 | H | — | Cl | 3-Cl | CH₃ | 0 | | |
| 12.065 | H | O | CH₃ | 3-CH₃ | CH₃ | 0 | | |
| 12.066 | H | O | CH₃ | 3-CH₃ | CH₃ | 0 | | Na salt |
| 12.067 | H | O | CH₃ | 3-CH₃ | CH₃ | 1 | | |
| 12.068 | H | O | CH₃ | 3-CH₃ | CH₃ | 1 | | Na salt |
| 12.069 | H | NH | CH₃ | 3-CH₃ | CH₃ | 0 | | |
| 12.070 | H | NH | CH₃ | 3-CH₃ | CH₃ | 0 | | Na salt |
| 12.071 | H | NH | CH₃ | 3-CH₃ | CH₃ | 1 | | |
| 12.072 | H | NH | CH₃ | 3-CH₃ | CH₃ | 1 | | Na salt |
| 12.073 | H | NCH₃ | CH₃ | 3-CH₃ | CH₃ | 0 | 128 decomp. | |
| 12.074 | H | NCH₃ | CH₃ | 3-CH₃ | CH₃ | 0 | | Na salt |
| 12.075 | H | NCH₃ | CH₃ | 3-CH₃ | CH₃ | 1 | | |
| 12.076 | H | NCH₃ | CH₃ | 3-CH₃ | CH₃ | 1 | | Na salt |
| 12.077 | H | — | F | 3-CH₃ | CH₃ | 0 | | |
| 12.078 | H | — | F | 3-CH₃ | CH₃ | 0 | | Na salt |
| 12.079 | H | — | F | 3-CH₃ | CH₃ | 1 | | |
| 12.080 | H | — | F | 3-CH₃ | CH₃ | 1 | | Na salt |
| 12.081 | H | — | Cl | 3-CH₃ | CH₃ | 0 | | |
| 12.082 | H | O | CH₃ | 4-Cl | CH₃ | 0 | | |
| 12.083 | H | O | CH₃ | 4-Cl | CH₃ | 0 | | Na salt |
| 12.084 | H | O | CH₃ | 4-Cl | CH₃ | 1 | | |
| 12.085 | H | O | CH₃ | 4-Cl | CH₃ | 1 | | Na salt |
| 12.086 | H | NH | CH₃ | 4-Cl | CH₃ | 0 | | |
| 12.087 | H | NH | CH₃ | 4-Cl | CH₃ | 0 | | Na salt |
| 12.088 | H | NH | CH₃ | 4-Cl | CH₃ | 1 | | |
| 12.089 | H | NH | CH₃ | 4-Cl | CH₃ | 1 | | Na salt |
| 12.090 | H | NCH₃ | CH₃ | 4-Cl | CH₃ | 0 | | |
| 12.091 | H | NCH₃ | CH₃ | 4-Cl | CH₃ | 0 | | Na salt |
| 12.092 | H | NCH₃ | CH₃ | 4-Cl | CH₃ | 1 | 100 decomp. | |
| 12.093 | H | NCH₃ | CH₃ | 4-Cl | CH₃ | 1 | 165 decomp. | Na salt |
| 12.094 | H | — | F | 4-Cl | CH₃ | 0 | | |
| 12.095 | H | O | C₂H₅ | — | CH₃ | 1 | 139 decomp. | Na salt |
| 12.096 | H | NCH₃ | CH₃ | — | C₂H₅ | 0 | 130–135 decomp. | |
| 12.097 | H | NCH₃ | CH₃ | — | CH₃ | 1 | 175 decomp. | Na salt |
| 12.098 | H | O | CH₃ | 4-CH₃ | CH₃ | 1 | | |
| 12.099 | H | O | CH₃ | 4-CH₃ | CH₃ | 1 | | |
| 12.100 | H | O | CH₃ | 4-OCH₃ | CH₃ | 1 | | |
| 12.101 | H | NH | CH₃ | 4-OCH₃ | CH₃ | 1 | | |
| 12.102 | H | NCH₃ | CH₃ | 4-OCH₃ | CH₃ | 1 | | |
| 12.103 | H | O | CH₃ | 4-OCH₃ | CH₃ | 0 | | |
| 12.104 | H | NH | CH₃ | 4-OCH₃ | CH₃ | 0 | | |
| 12.105 | H | NCH₃ | CH₃ | 4-OCH₃ | CH₃ | 0 | | |

USE EXAMPLES

A Herbicidal action

The herbicidal action of the sulfonylureas of the formula I can be demonstrated by greenhouse experiments.

The culture vessels used were plastic flower pots containing loamy sand with about 3.0% of humus as a substrate. The seeds of the test plants were sown separately according to species.

In the preemergence treatment, the active ingredients, suspended or emulsified in water, were applied directly after sowing, by means of finely distributing nozzles. The vessels were lightly watered in order to promote germination and growth and were then covered with transparent plastic covers until the plants had begun to grow. This covering ensures uniform germination of the test plants, unless this has been adversely affected by the active ingredients. The application rates were 0.125 kg/ha of active substance.

For the postemergence treatment, the test plants were treated with the active ingredients suspended or emulsified in water, at a height of growth of from 3 to 15 cm, depending on the form of growth. The application rate for the postemergence treatment was 0.125 kg/ha of active substance.

The plants were kept at 10°–25° C. or 20°–35° C., depending on the species. The test period extended over from 2 to 4 weeks. During this time, the plants were tended and their reaction to the individual treatments was evaluated.

Evaluation was based on a scale from 0 to 100. 100 means no emergence of the plants or complete destruction of at least the above-ground parts and 0 means no damage or normal growth.

The plants used in the greenhouse experiments consisted of the following species:

| Abbreviation | Botanical name | Common name |
|---|---|---|
| AMARE | *Amaranthus retroflexus* | redroot pigweed |
| GALAP | *Galium aparine* | catchweed |
| POLPE | *Polygonum persicaria* | lady's-thumb |
| TRZAW | *Triticum aestivum* | winter wheat |

When 0.125 kg/ha of active substance is used in the preemergence and postemergence method, undesirable broadleaved plants can be very readily controlled with Example 5.019, which is furthermore tolerated by wheat.

B Bioregulatory action
B.1 Growth regulatory action

To determine the growth-regulating properties of the candidate compounds, test plants were grown in plastic pots approx. 12.5 cm in diameter in a substrate provided with sufficient nutrients.

The candidate compounds were sprayed postemergence onto the plants as aqueous formulations. The growth-regulating action observed was confirmed at the end of the experiment by measuring the height of the plants. The figures obtained were compared with the growth height of the untreated plants. The agent used for comparative purposes (A) was 2-chloroethyl-trimethylammonium chloride (CCC).

The reduction in growth height was also accompanied by a deeper leaf coloration. The increased chlorophyll content is indicative of an increased rate of photosynthesis, making for bigger yields.

The individual data are given in the tables below.

TABLE B.1.1

| | Spring wheat, "Ralle" Postemergence (leaf) treatment | |
|---|---|---|
| Compound | Concentration (mg of active ingredient/vessel) | Growth height (relative) |
| Untreated | — | 100 |
| A | 0.38 | 91.4 |
| | 1.5 | 86.3 |
| 12.032 | 0.38 | 67.3 |
| | 1.5 | 45.7 |

TABLE B.1.2

| | Spring barley, "Aramir" Postemergence (leaf) treatment | |
|---|---|---|
| Compound | Concentration (mg of active ingredient/vessel) | Growth height (relative) |
| Untreated | — | 100 |
| A | 0.38 | 100 |
| | 1.5 | 92.9 |
| 12.032 | 0.38 | 69.3 |
| | 1.5 | 51.3 |

TABLE B.1.3

| | Spring rape, "Petranova" Postemergence (leaf) treatment | |
|---|---|---|
| Compound | Concentration (mg of active ingredient/vessel) | Growth height (relative) |
| Untreated | — | 100 |
| A | 0.025 | 99.4 |
| | 0.1 | 94.3 |
| 12.032 | 0.025 | 72.4 |
| | 0.1 | 60.6 |

B.2 Defoliant action in cotton

The leaves of young cotton plants (Stoneville 825 variety; development stage: 5-6 true leaves) were grown under greenhouse conditions (day/night) temperature: 25°/18° C.; relative humidity: 50-70%) were sprayed to runoff with aqueous formulations of the candidate compounds (with the addition of 0.15 wt%, based on the spray liquor, of the fatty alcohol alkoxylate Plurafac ® LF 700). The amount of water used was equivalent to 1,000 liters per hectare. 13 days after the active ingredients had been applied, the number of cast-off leaves was determined; the degree of defoliation is given in %, relative tot he control. No leaves dropped from the untreated control plants. The comparative agent B was 6,7-dihydrodipyridol (1,2-:2',1'-c) pyridilium ion as dibromide monohydrate salt (diquat). The results are given in Table B.2.1.

TABLE B.2.1

| Agent containing active ingredient no. | Application rate converted to kg/ha | Defoliation in % |
|---|---|---|
| 5.019 | 0.25 | 49 |
| | 0.50 | 64 |
| 12.027 | 0.25 | 31 |
| | 0.50 | 31 |
| Comparative agent B | 0.50 | 36 |

What is more, the agents according to the invention reduce re-sprouting of the plants after defoliation. This effect facilitates machine harvesting of the cotton plants.

We claim:

1. A member selected from the group consisting of a substituted sulfonylurea of the formula I

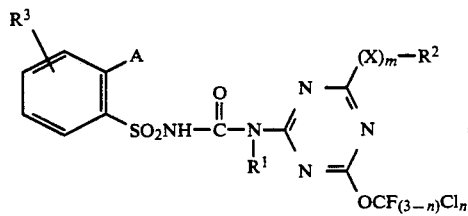

where
n is 1 and m is 0 or 1 and the substituents have the following meanings:
$R^1$ is hydrogen, $C_1$–$C_4$-alkyl, $C_3$–$C_6$-alkenyl or $C_3$–$C_6$-alkynyl;
$R^2$ is halogen or trifluoromethyl when m is 0, or $C_1$–$C_4$-alkyl, $C_3$–$C_6$-alkenyl or $C_3$–$C_6$-alkynyl when m is 1, or trifluoromethyl or chlorodifluoromethyl when X is O or S and m is 1;
X is O, S or N-$R^4$, where $R^4$ is hydrogen or $C_1$–$C_4$-alkyl;
$R^3$ is hydrogen, halogen, $C_1$–$C_4$-alkyl, $C_1$–$C_4$-haloalkyl or $C_1$–$C_4$-alkoxy;
A is $C_1$–$C_4$-haloalkyl, halogen, CN, $NO_2$, $C_1$–$C_4$-alkoxy, $C_1$–$C_4$-alkylthio;
$C_1$–$C_4$-alkylsulfinyl- or -sulfonyl or a radical

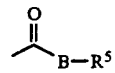

where
B is oxygen or an alkylimino group N-$R^6$;
$R^5$ is hydrogen, $C_1$–$C_6$-alkyl which may carry up to three of the following radicals: halogen, $C_1$–$C_4$- alkoxy, $C_1$–$C_4$-alkylthio, $C_1$–$C_4$-haloalkoxy, $C_2$–$C_4$-alkoxy-$C_1$–$C_2$-alkoxy, $C_3$–$C_7$-cycloalkyl and/or phenyl;

$C_5$–$C_7$-cycloalkyl which may carry up to three $C_1$–$C_4$-alkyl groups;

$C_3$–$C_6$-alkenyl or $C_3$–$C_6$-alkynyl, and $R^6$ is hydrogen or $C_1$–$C_6$-alkyl, or, together with $R^5$, forms tetramethylene, pentamethylene, hexamethylene, ethyleneoxyethylene, or ethylene-N-methyliminoethylene, and environmentally compatible salts thereof.

2. A sulfonylurea as set forth in claim 1, where the substituents have the following meanings:

$R^1$ is hydrogen or methyl;

$R^2$ is methyl when m is 1;

X is O or NH;

$R^3$ is hydrogen, halogen or methyl and

A is a group $CO_2R^5$, where $R^5$ is $C_1$–$C_4$-alkyl.

3. A herbicidal composition which comprises a sulfonylurea of the formula I as set forth in claim 1, or a salt thereof, and conventional carriers therefor.

4. A method for combating the growth of unwanted plants, wherein a herbicidally effective amount of a sulfonylurea of the formula I as set forth in claim 1, or of a salt thereof, is allowed to act on the plants and/or their habitat.

5. A method for combating the growth of unwanted plants in cereals, wherein a herbicidally effective amount of methyl 2-(((4-methoxy-6-chlorodifluoromethoxy-1,3,5-triazin-2-yl)-aminocarbonyl)aminosulfonyl)benzoate is employed.

6. A method for regulating the growth of plants, wherein a growth-regulatory amount of a sulfonylurea of the formula I as set forth in claim 1, or of a salt thereof, is allowed to act on the seeds, the plants and/or their habitat.

* * * * *